United States Patent [19]

Rubinsky et al.

[11] Patent Number: 5,706,810
[45] Date of Patent: Jan. 13, 1998

[54] MAGNETIC RESONANCE IMAGING ASSISTED CRYOSURGERY

[75] Inventors: Boris Rubinsky, Albany; John Gilbert, Berkeley; San Wong, Emeryville; Mark Roos, San Francisco; Grant Pease, Oakland, all of Calif.

[73] Assignee: The Regents of the University of California, Oakland, Calif.

[21] Appl. No.: 461,253

[22] Filed: Jun. 2, 1995

Related U.S. Application Data

[62] Division of Ser. No. 35,455, Mar. 23, 1993, Pat. No. 5,433,717.

[51] Int. Cl.[6] .................................................. A61B 5/055
[52] U.S. Cl. ......................................... 128/653.1; 128/736
[58] Field of Search ................................. 128/736, 653.1; 324/315; 606/20, 21

[56] References Cited

U.S. PATENT DOCUMENTS

| | | |
|---|---|---|
| 3,228,400 | 1/1966 | Armao . |
| 3,618,610 | 11/1971 | Hannant . |
| 3,662,755 | 5/1972 | Rautenbach et al. . |
| 3,674,031 | 7/1972 | Weiche . |
| 3,800,552 | 4/1974 | Sollami et al. . |
| 3,807,403 | 4/1974 | Stumpf et al. . |
| 3,886,945 | 6/1975 | Stumpf et al. . |
| 3,901,241 | 8/1975 | Allen, Jr. . |
| 3,942,519 | 3/1976 | Shock . |
| 3,971,383 | 7/1976 | van Gerven et al. . |
| 4,206,609 | 6/1980 | Durenec . |
| 4,207,897 | 6/1980 | Lloyd et al. . |
| 4,341,220 | 7/1982 | Perry . |
| 4,345,598 | 8/1982 | Zobac et al. . |
| 4,528,979 | 7/1985 | Marchenko et al. . |
| 4,554,925 | 11/1985 | Young . |
| 4,558,279 | 12/1985 | Ackerman et al. .......... 324/315 |

(List continued on next page.)

FOREIGN PATENT DOCUMENTS

| | | |
|---|---|---|
| 0095124 | 11/1983 | European Pat. Off. . |
| 0343858 | 11/1989 | European Pat. Off. . |
| 1249416 | 8/1986 | U.S.S.R. . |
| 9107132 | 5/1991 | WIPO . |

OTHER PUBLICATIONS

Rubinsky, et al., "Monitoring Cryosurgery . . . ", *Cryobiology*, vol. 30, pp. 191–199, Apr. 1993.

Matsumoto, R., et al., "Monitoring of Laser and Freezing-induced Ablation in the Liver with T1-weighted MR Imaging", *Journal of Magnetic Resonance Imaging*, vol. 2, p. 555, 1992.

Hurst, G.G. et al., "Intravascular (Catheter) NMR Receiver Probe: Preliminary Design Analysis and Application to Canine Iliofemoral Imaging", *Magnetic Resonance in Medicine*, vol. 24, p. 343, (1992).

(List continued on next page.)

*Primary Examiner*—William E. Kamm
*Assistant Examiner*—George R. Evanisko
*Attorney, Agent, or Firm*—Fish & Richardson P.C.

[57] ABSTRACT

Methods and apparatus for magnetic resonance imaging (MRI) assisted cryosurgery. Optimal probe placements and cooling parameters are calculated prior to cryosurgery using MRI data. A MRI compatible cryoprobe and a stereotactic probe positioning device are provided. The resolution of MR images is enhanced by mounting a radio frequency MR coil on the intracorporeal end of a cryoprobe. During cryosurgery the temperature distribution in the frozen region is solved by determining the boundary of the frozen region and solving the heat equation for the known boundary conditions. During cryosurgery the temperature distribution in the unfrozen region is determined by T1 measurements. The process of freezing is controlled using information from the solution of the energy equation in the frozen region and temperature measurements in the unfrozen region. After cryosurgery the extent of the tissue damage may be ascertained using phosphorus-31 and/or sodium-23 spectroscopy with a special coil set on the cryosurgical probe.

14 Claims, 14 Drawing Sheets

U.S. PATENT DOCUMENTS

| | | |
|---|---|---|
| 4,583,538 | 4/1986 | Onik et al. . |
| 4,618,978 | 10/1986 | Cosman . |
| 4,724,389 | 2/1988 | Hyde et al. . |
| 4,740,751 | 4/1988 | Misic et al. . |
| 4,770,171 | 9/1988 | Sweren et al. . |
| 4,785,246 | 11/1988 | Sugimoto . |
| 4,831,330 | 5/1989 | Takahashi . |
| 4,869,247 | 9/1989 | Howard, III et al. . |
| 4,882,541 | 11/1989 | Haragashira . |
| 4,890,062 | 12/1989 | Haragashira . |
| 4,923,459 | 5/1990 | Nambu . |
| 4,946,460 | 8/1990 | Merry et al. ............................. 606/24 |
| 5,046,498 | 9/1991 | Fishman ............................. 128/653.2 |
| 5,050,607 | 9/1991 | Bradley et al. ....................... 128/653.2 |
| 5,050,608 | 9/1991 | Watanabe et al. . |
| 5,078,713 | 1/1992 | Varney et al. . |
| 5,108,390 | 4/1992 | Potocky et al. ............................ 606/21 |
| 5,196,348 | 3/1993 | Schweighardt et al. ............. 178/653.4 |
| 5,200,345 | 4/1993 | Young ................................. 178/653.1 |
| 5,205,289 | 4/1993 | Hardy et al. .......................... 128/653.1 |
| 5,254,116 | 10/1993 | Baust et al. ................................ 606/21 |
| 5,281,215 | 1/1994 | Milder ....................................... 606/20 |
| 5,290,266 | 3/1994 | Rohling et al. ....................... 128/653.2 |
| 5,300,080 | 4/1994 | Clayman et al. ......................... 606/130 |
| 5,531,742 | 7/1996 | Barken ...................................... 606/21 |

OTHER PUBLICATIONS

Zemtsov, A., et al., "Magnetic Resonance Imaging of Cutaneous Neoplasms: Clinicopathological Correlation", *Journal of Dermatological Surgery and Oncology*, vol. 17, p. 416, 1991.

Zemtsov, A., et al., "Magnetic Resonance Imaging of Cutaneous Melanocytic Lesions", *Journal of Dermatological Surgery and Oncology*, vol. 15, pp. 854, 989.

Isoda, H., "Sequential MRI and CT Monitoring in Cryosurgery–An Experimental Study in Rats", *Nippon Acta Radiologica*, vol. 49, No. 12, p. 17, Dec. 25, 1989.

Isoda, H., "Sequential MRI and CT Monitoring in Cryosurgery–An Experimental Study in Polyvinyl Alcohol Gel Phantom", *Nippon Acta Radiologica*, vol. 49, No. 12, p. 6, Dec. 25, 1989.

Rubinsky, B., et al., "A mathematical model for the freezing process in biological tissue", *Proc. R. Soc. Lond.* B vol. 234, p. 343, 1988.

Rubinsky, B., et al., "Cryosurgery: advances in the application of low temperatures to medicine," *Rev. Int. Froid*, vol. 14, p. 1, 1991.

Rubinsky, B. et al., Heat Transfer During Freezing of Biological Materials, In: Tien ed. 1989, Hemisphere Publishing Corp. New York.

Keanini, R., et al., "Simulation and Optimization of Three–Dimensional Multi–Probe Prostatic Cryosurgery," *J. Heat Transfer*—ASME Trans., vol. 114, p. 796, 1992.

Onik, G., et al., "Ultrasound Guided Hepatic Cryosurgery in the Treatment of Metastic Colon Carcinoma; Preliminary Results," *Cancer*, vol. 67, p. 901, 1991.

Onik, G., et al., "Percutaneous Transperineal Prostate Cryosurgery Using Transrectal Ultrasound Guidance: Animal Model," *Urology* vol. 37, p. 277, 1991.

Dickinson, R. J., et al., "Measurement of Changes in Tissue Temperature using MR Imaging," *Joaurnal of Computer Assisted Tomography*, vol. 10, p. 468, 1986.

Le Bihan, D., et al., "Temperature Mapping with MR imaging of Molecular Diffusion: Application to Hyperthermia," *Radiology*, vol. 171, p. 853, 1989.

Gilbert, J. C., et al., "Solid–Liquid Interface Monitoring with Ultrasound During Cryosurgery," ASME Paper #85–WA/HT–83, 1985.

Bottomley et al., "A review of H NMR, relaxation in pathology; are T1 and T2 diagnostic?" *Mechanical Physics*, vol. 14, p. 1, 1987.

Mulkern et al., "Contrast Manipulation and Artifact Assessment of 3D and 4D RARE sequence," *Magnetic Resonance in Medicine* vol. 8, p. 557, 1990.

Vinning E. et al, "Magnetic Resonance Imaging of the Thalamus following Cryothalamotomy for Parkimson's Disease and Dystonia", *Journal of Neuroimaging*, vol. 1, No. 3, p. 146, Aug. 1991.

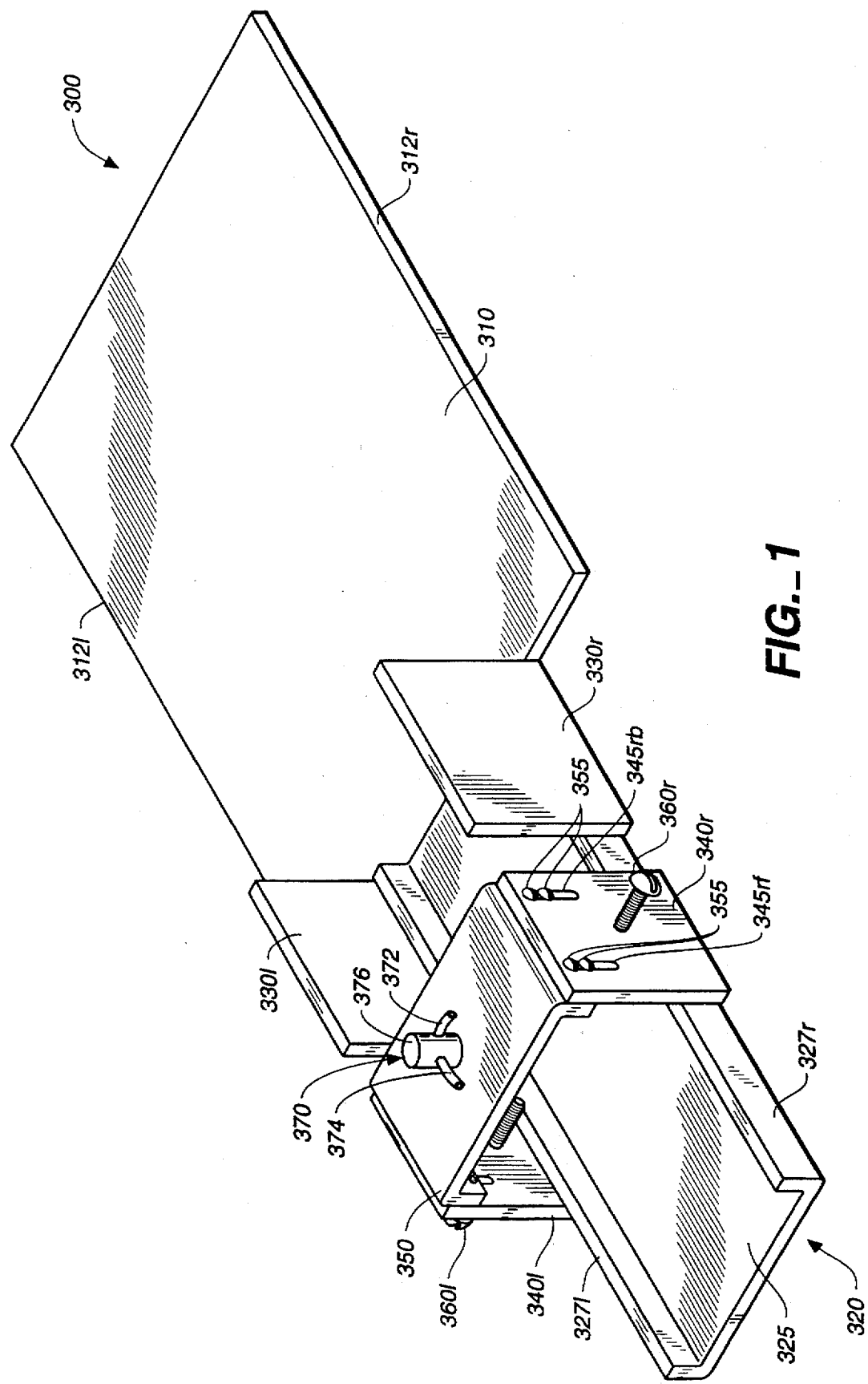
FIG._1

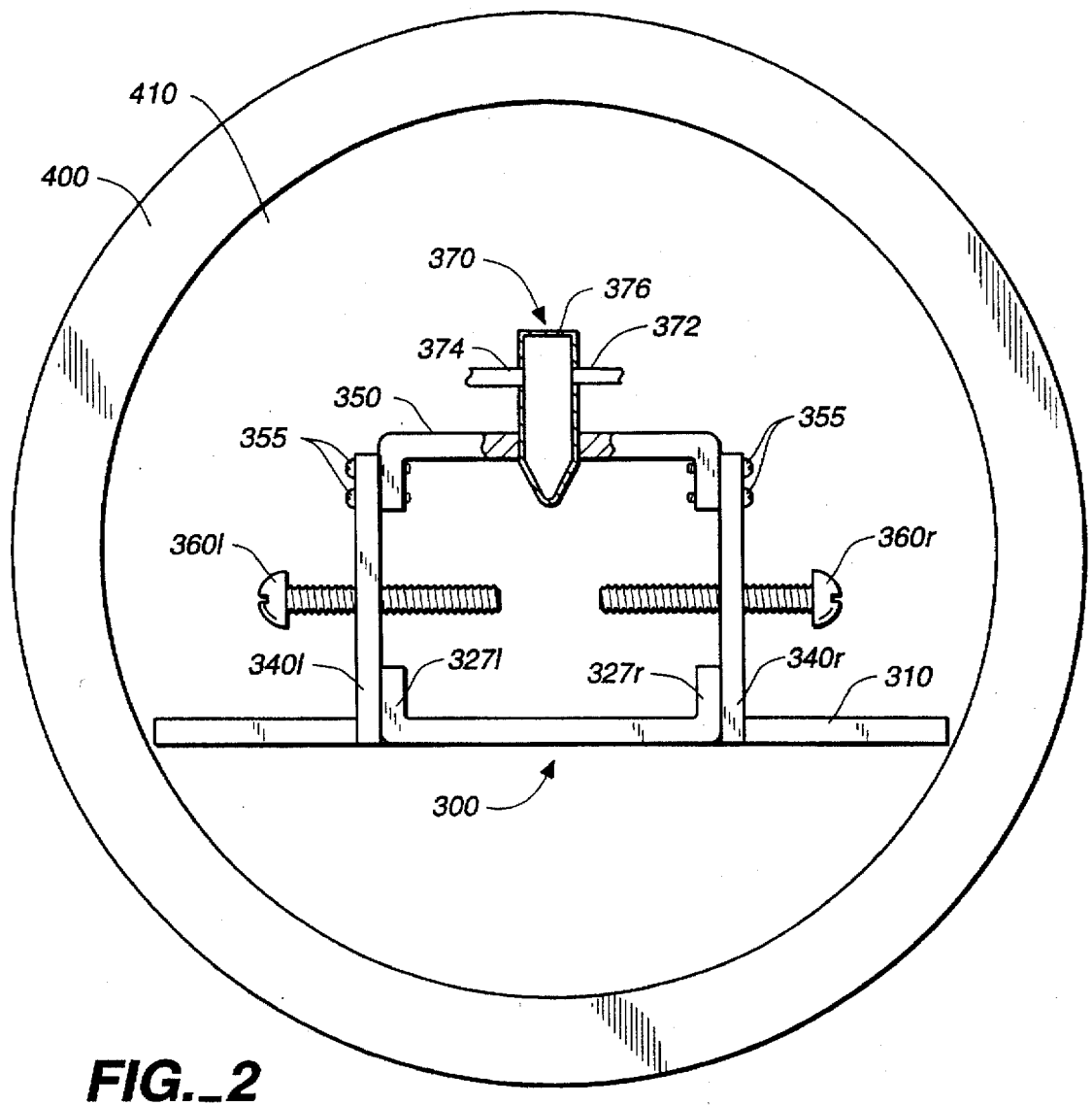
FIG._2

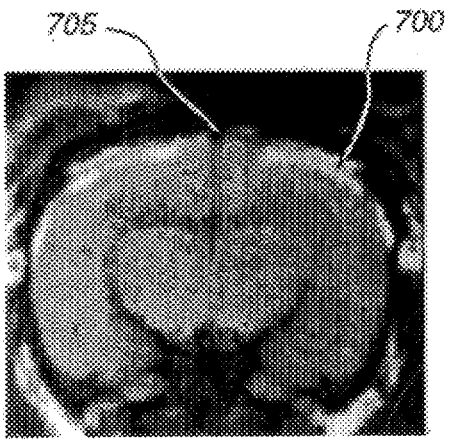
FIG._3A
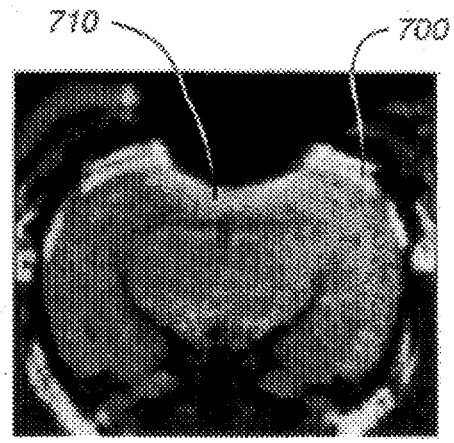
FIG._3B
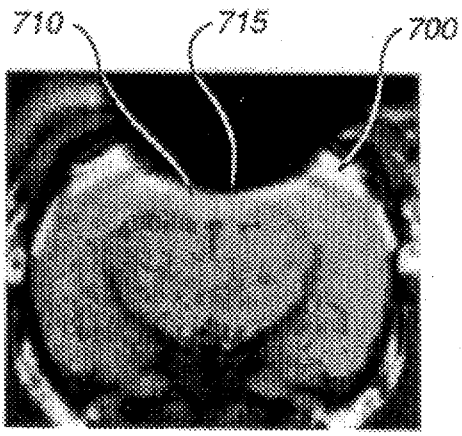
FIG._3C
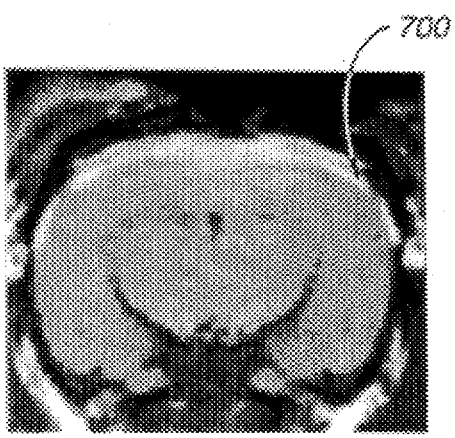
FIG._3D
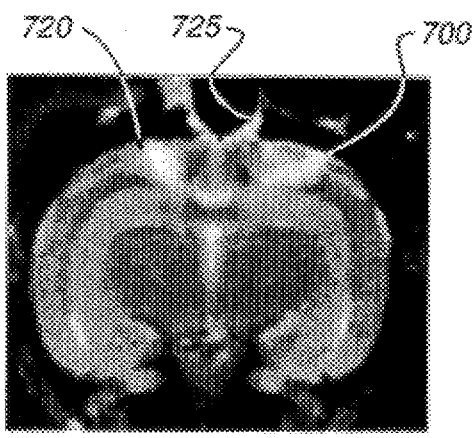
FIG._3E
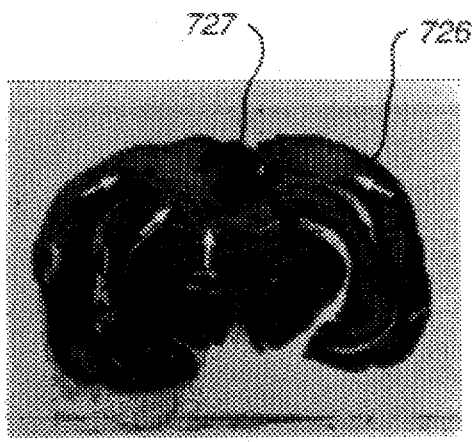
FIG._3F

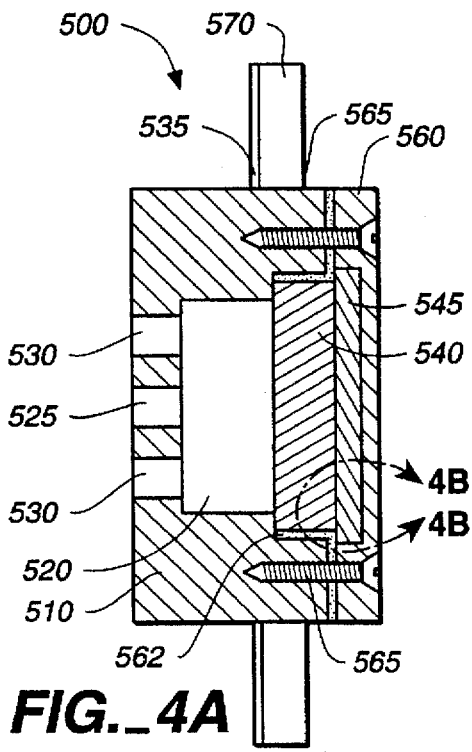
FIG._4A
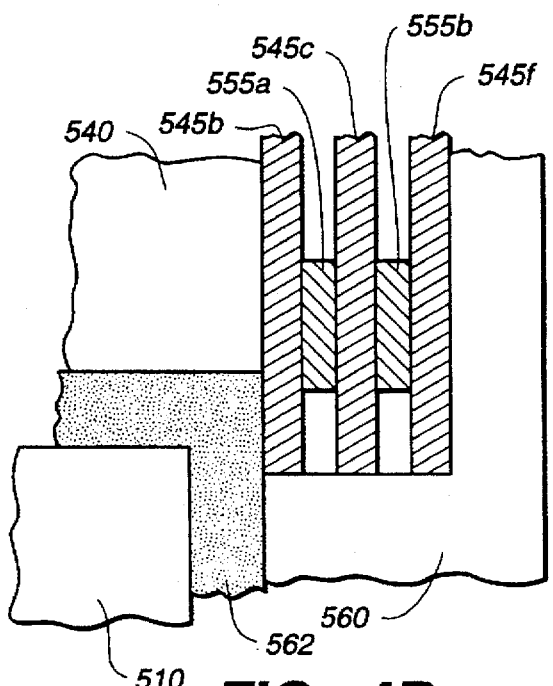
FIG._4B
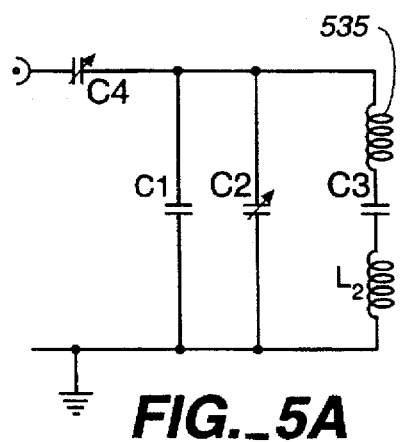
FIG._5A
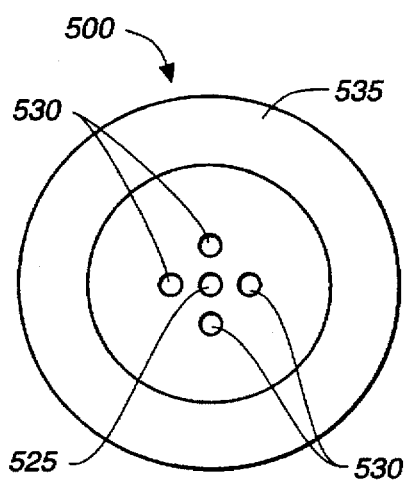
FIG._4C
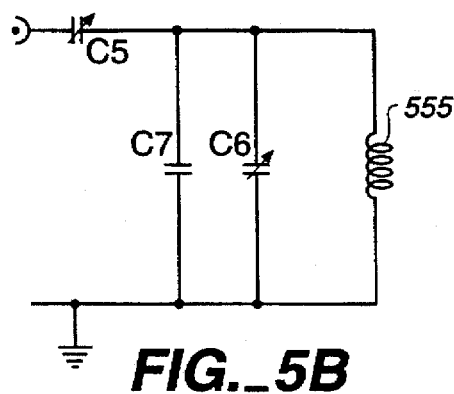
FIG._5B

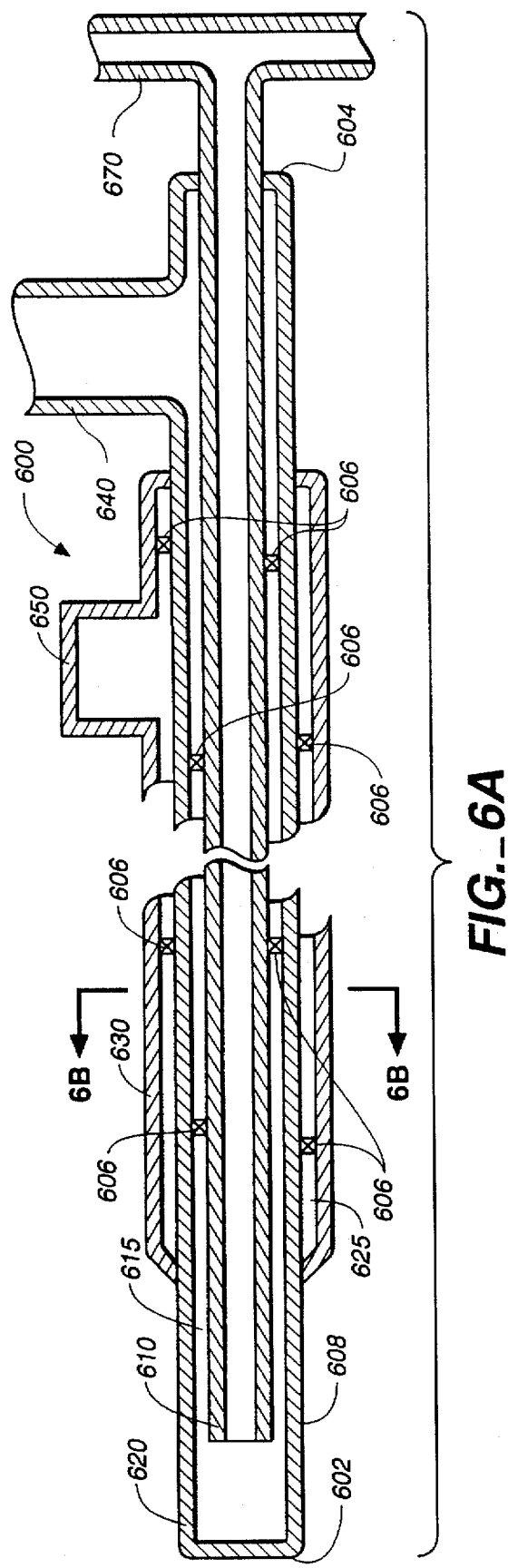
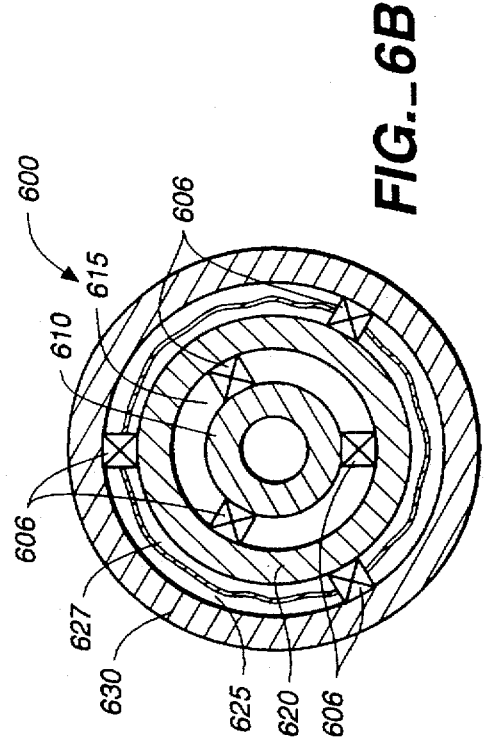

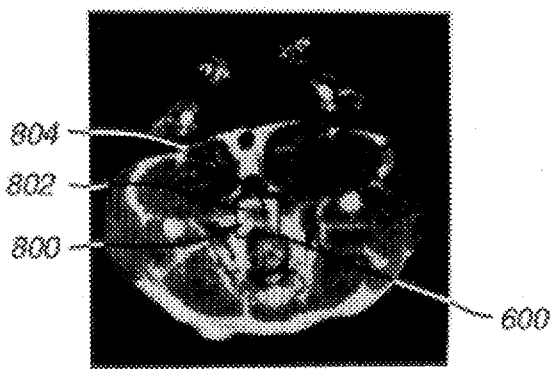
*FIG._7A*
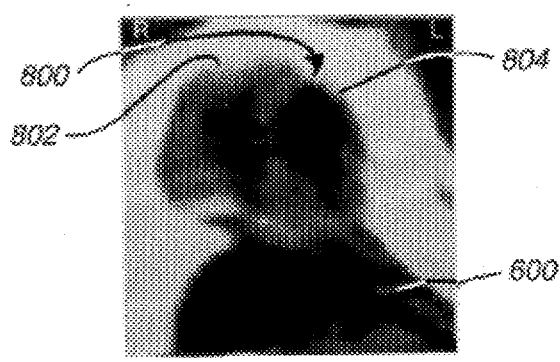
*FIG._7B*
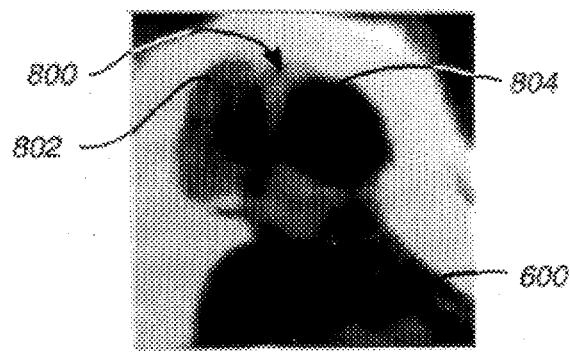
*FIG._7C*
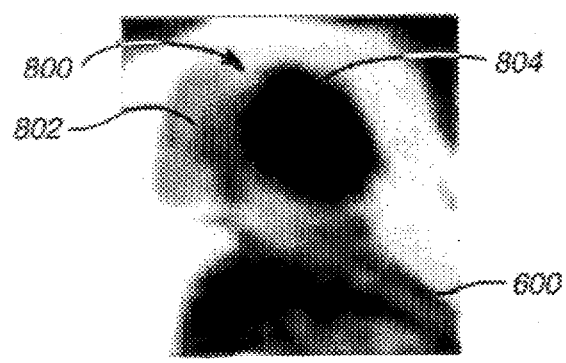
*FIG._7D*
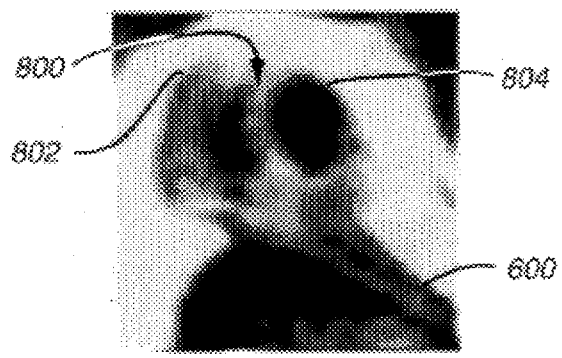
*FIG._7E*
*FIG._7F*
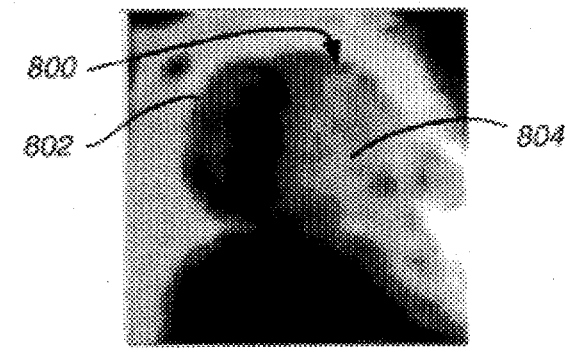
*FIG._7G*

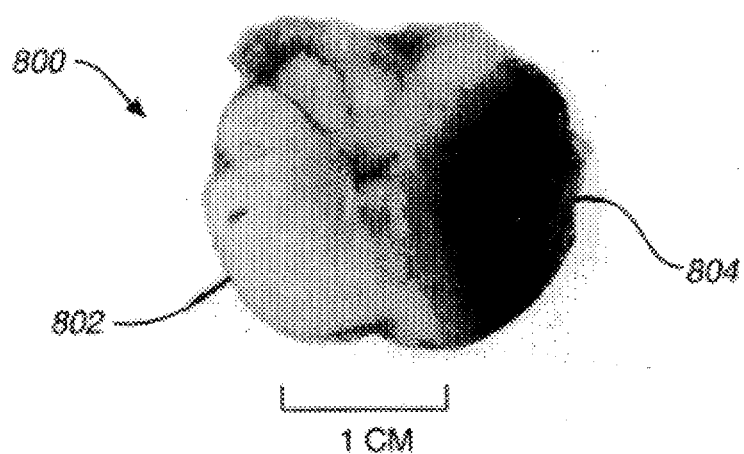
FIG._8A
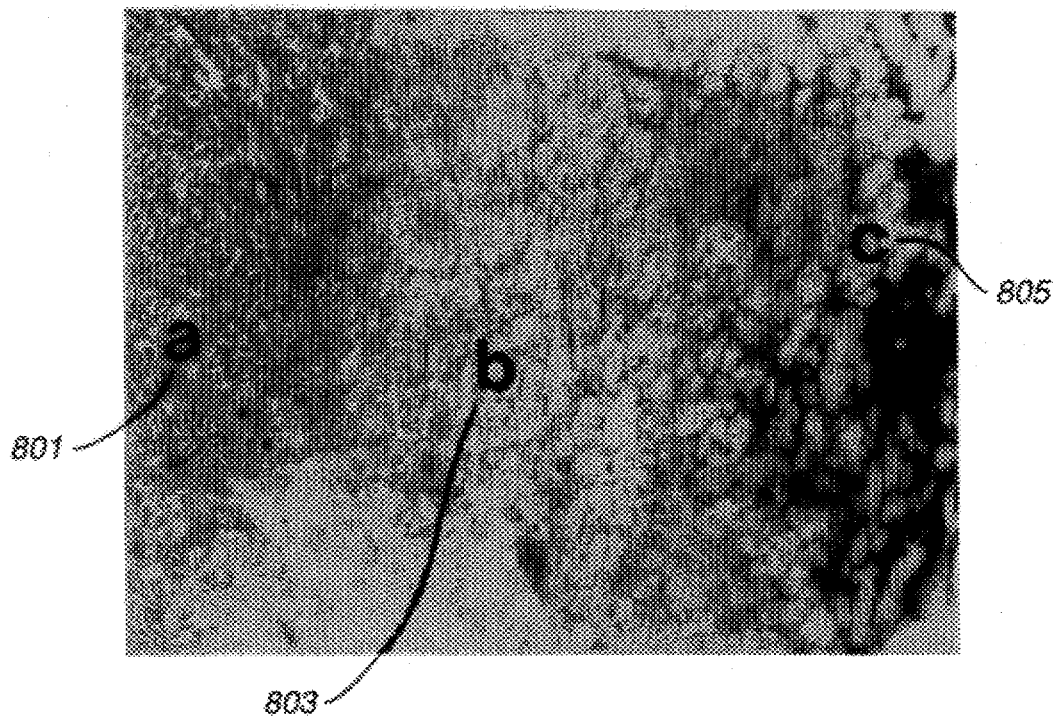
FIG._8B

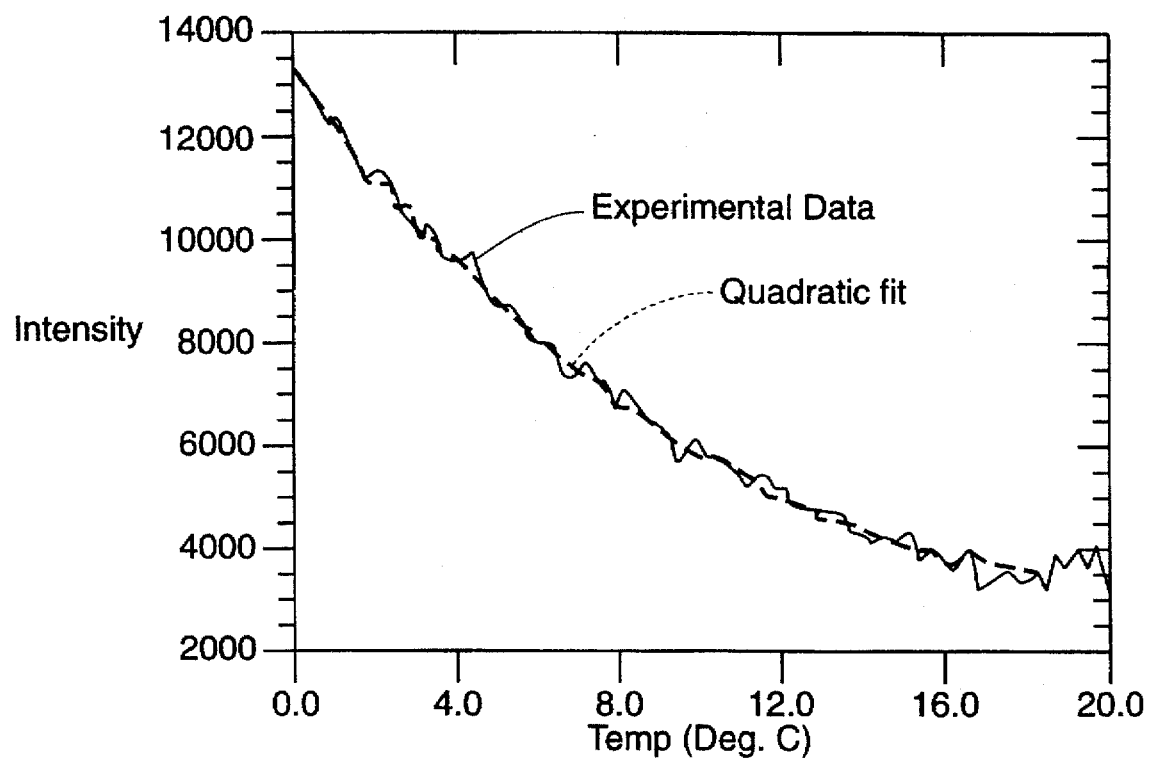
FIG._9

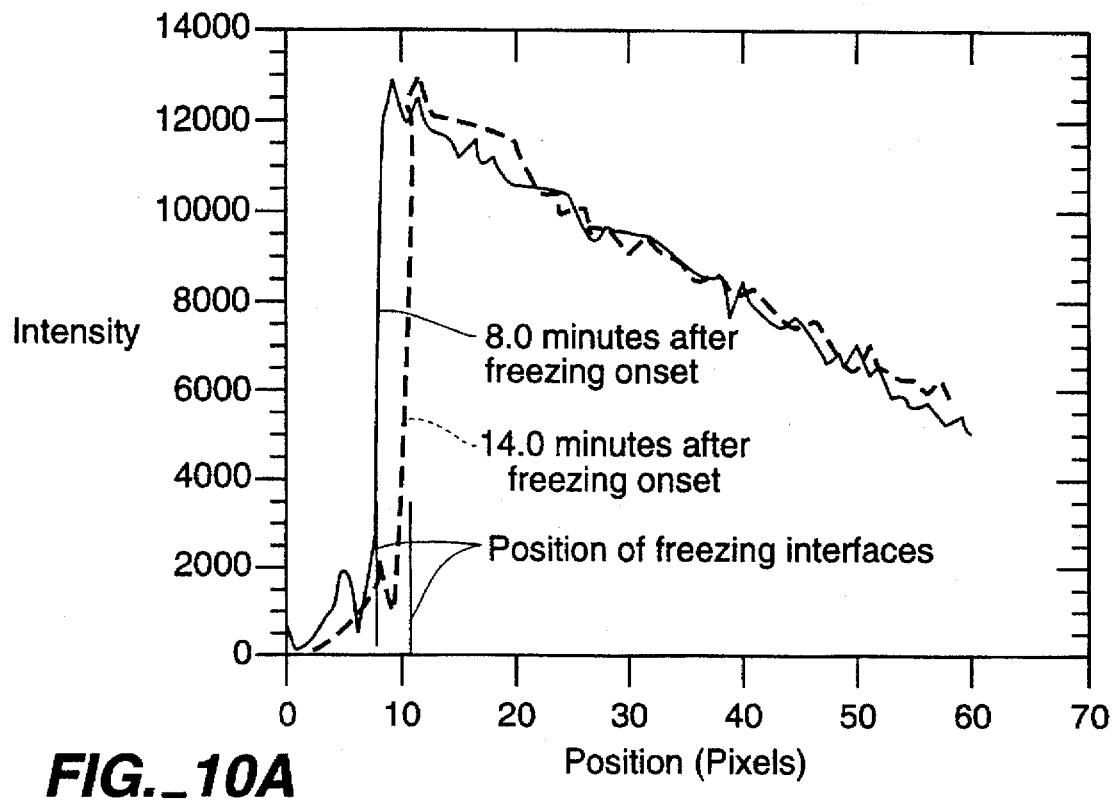
FIG._10A
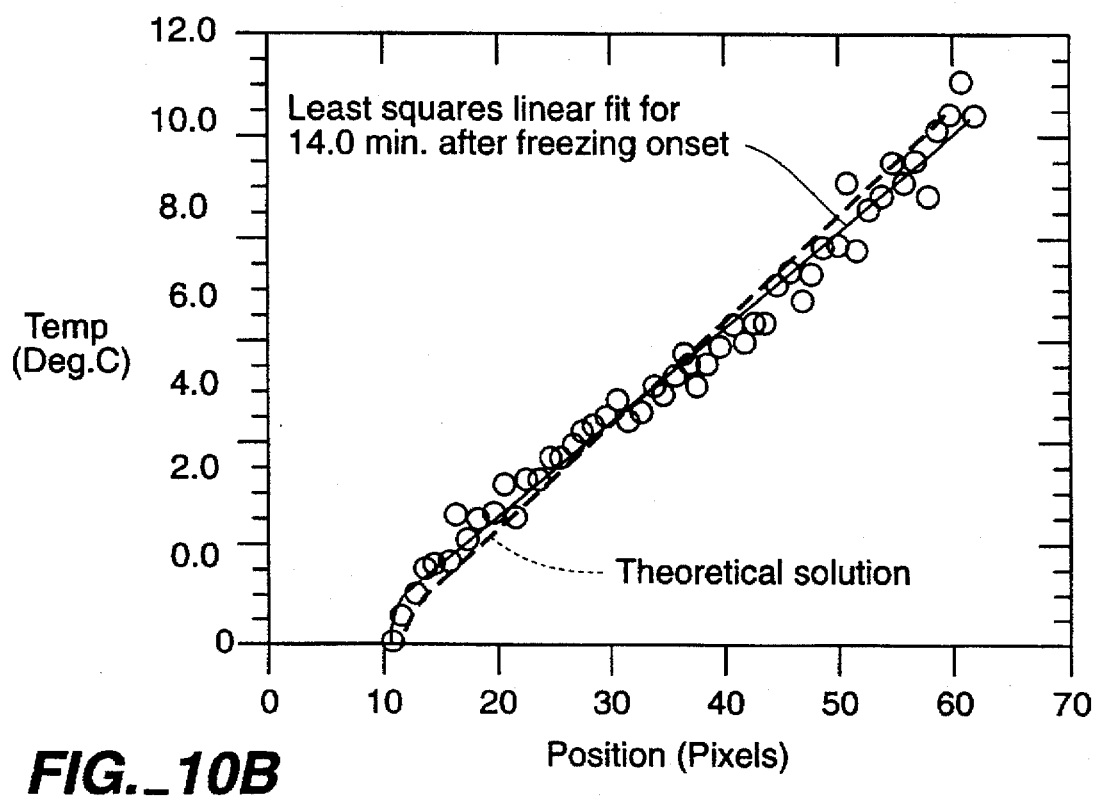
FIG._10B

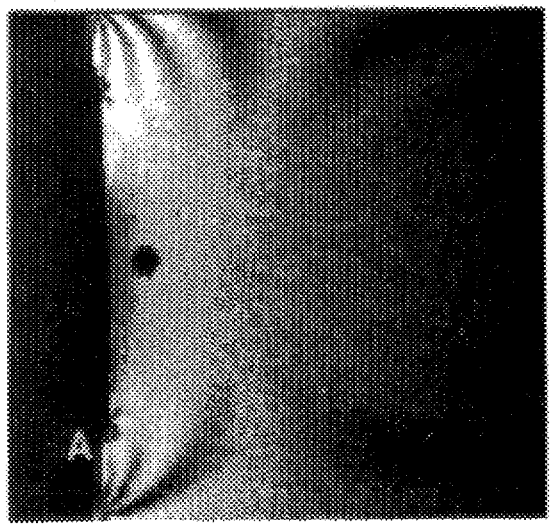
FIG._11A
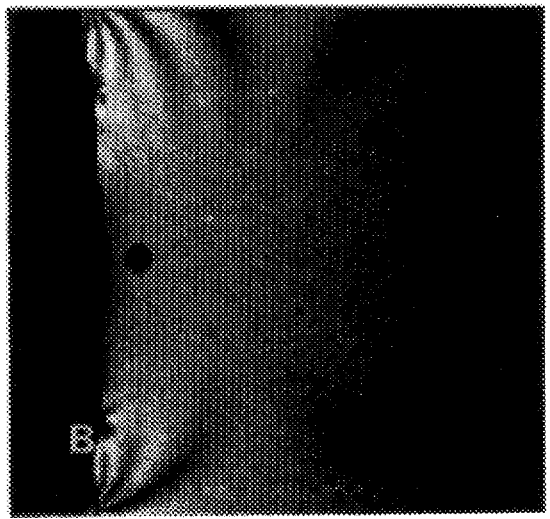
FIG._11B
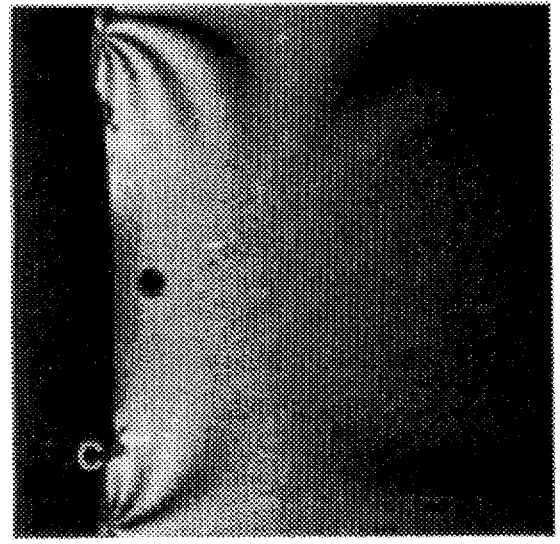
FIG._11C
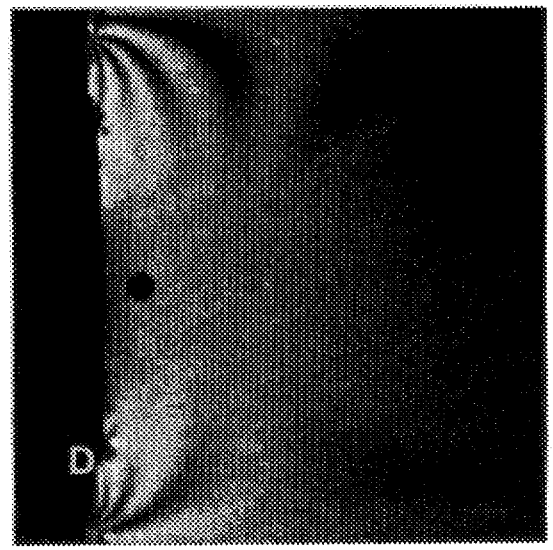
FIG._11D
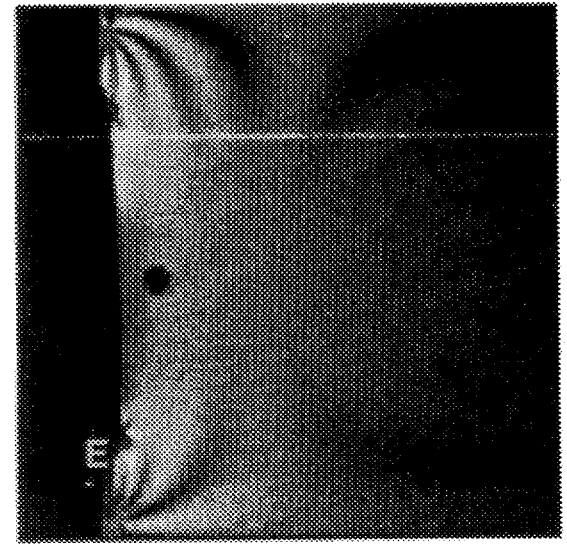
FIG._11E
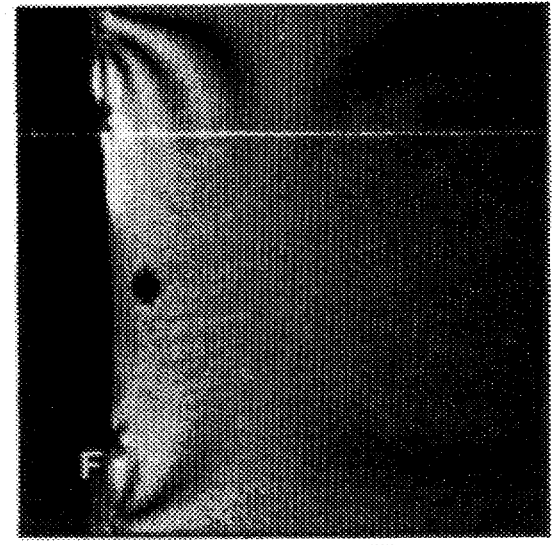
FIG._11F

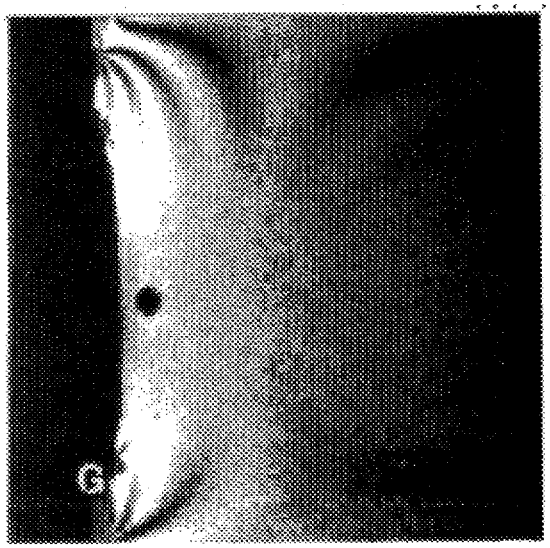
FIG._11G
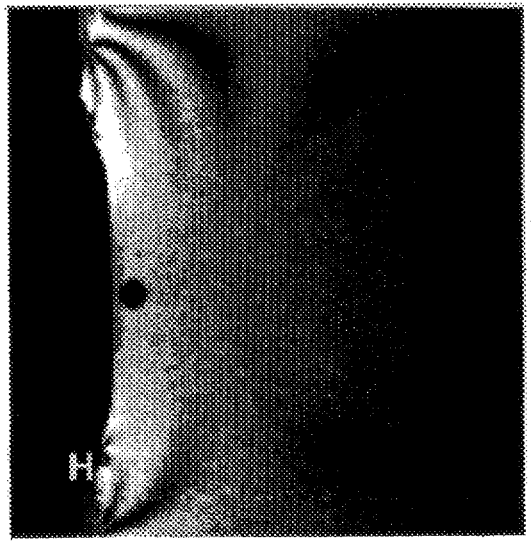
FIG._11H
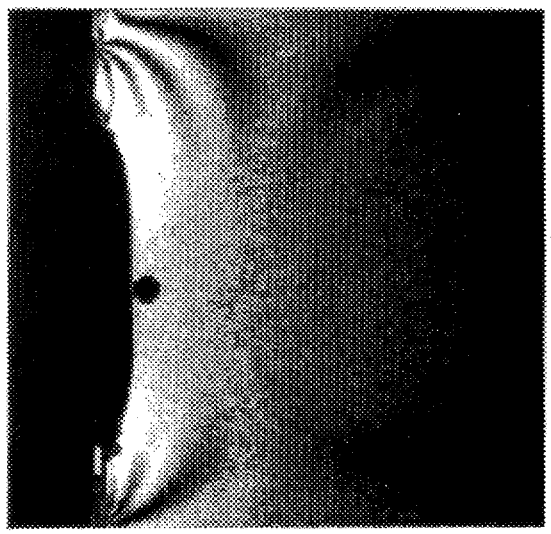
FIG._11I
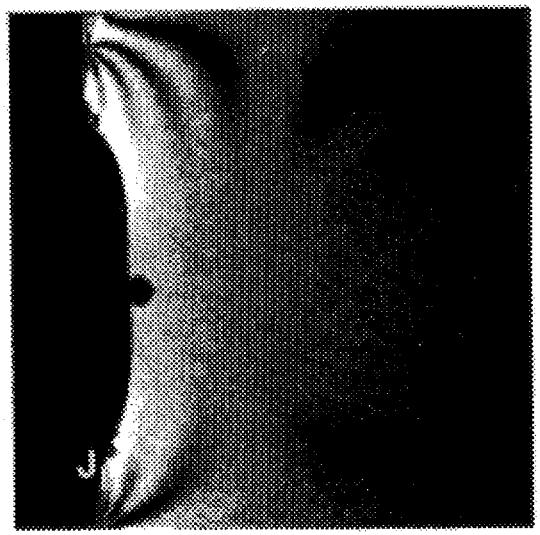
FIG._11J
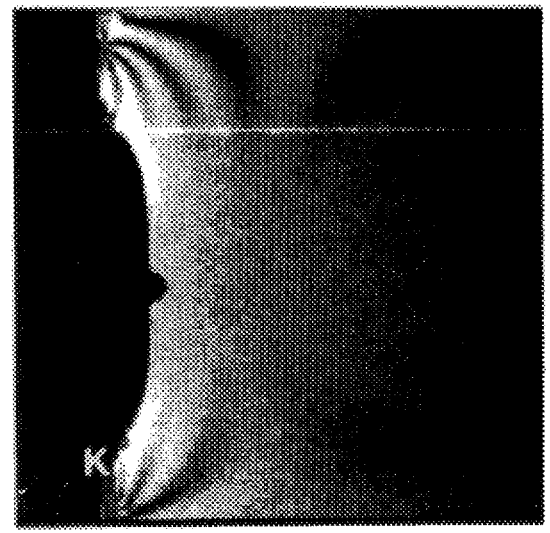
FIG._11K
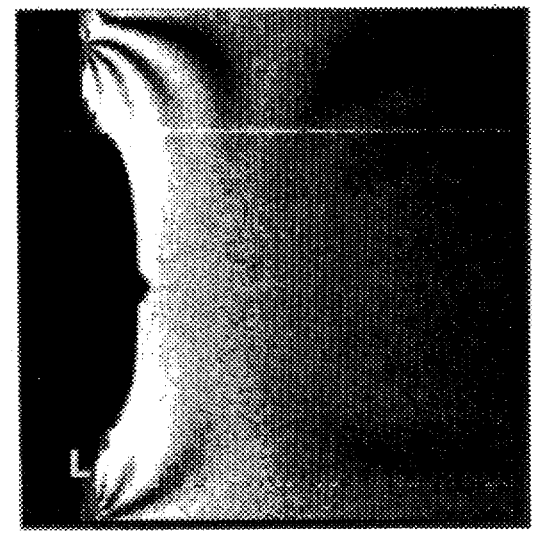
FIG._11L

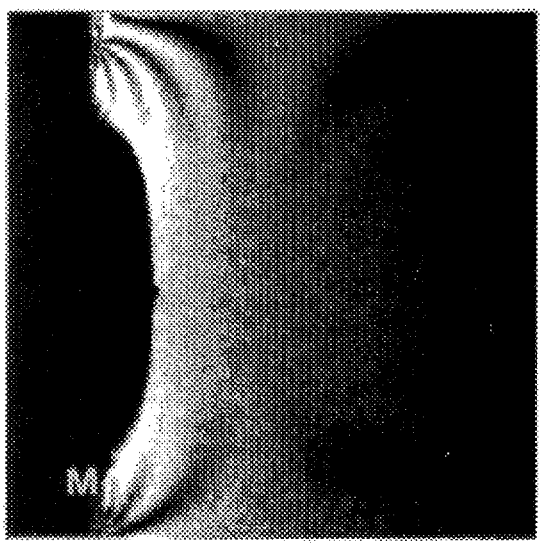
FIG._11M
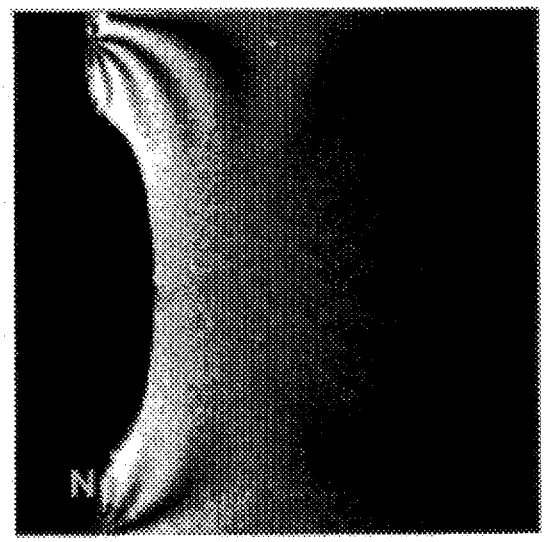
FIG._11N
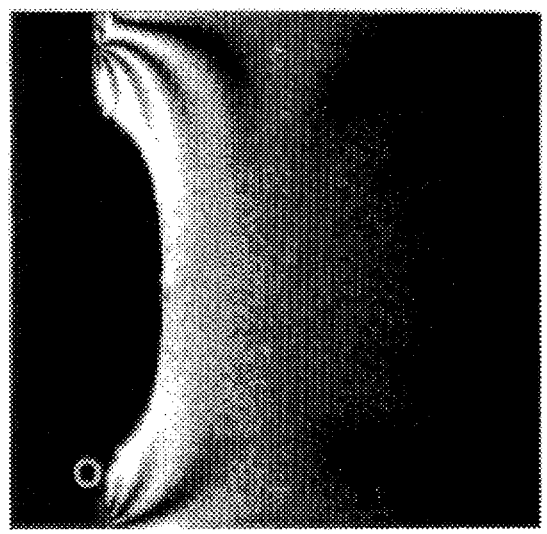
FIG._11O
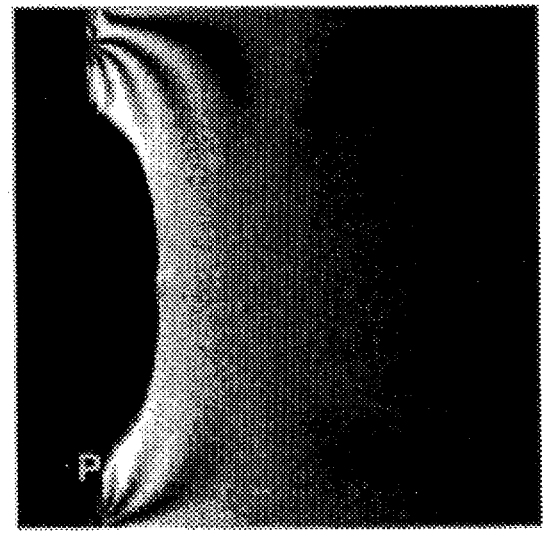
FIG._11P
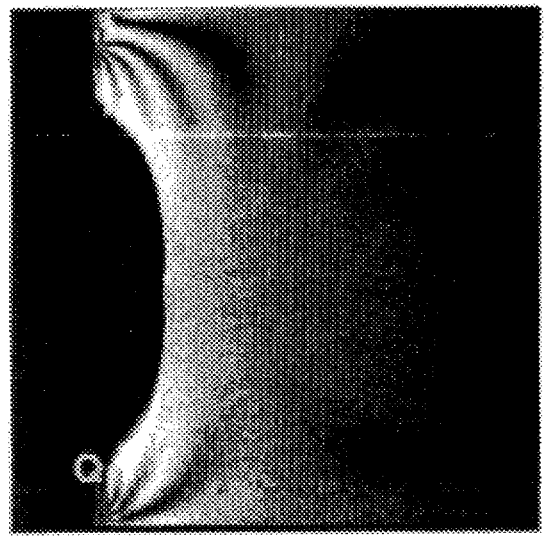
FIG._11Q
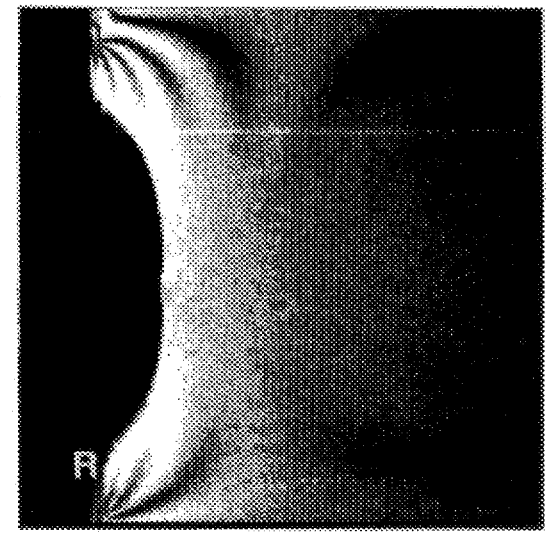
FIG._11R

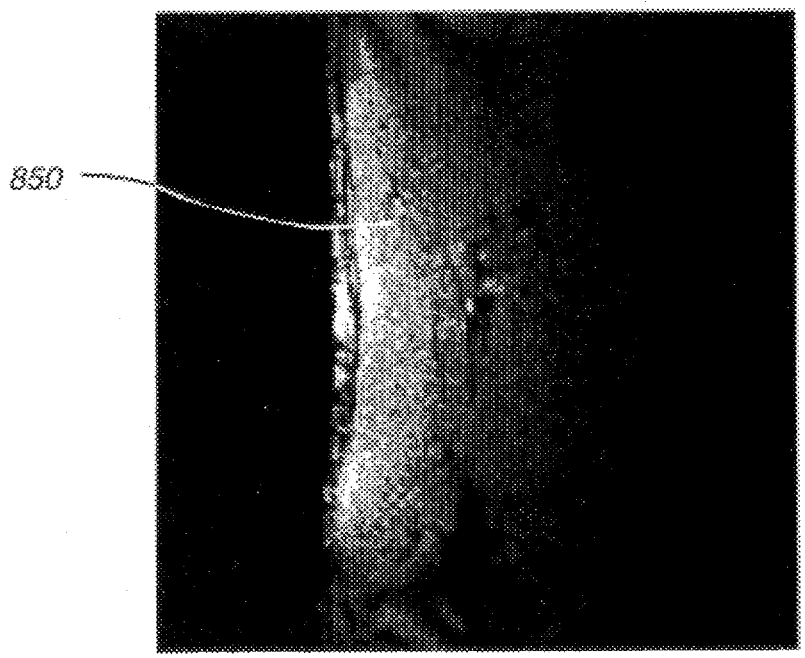
FIG._12A
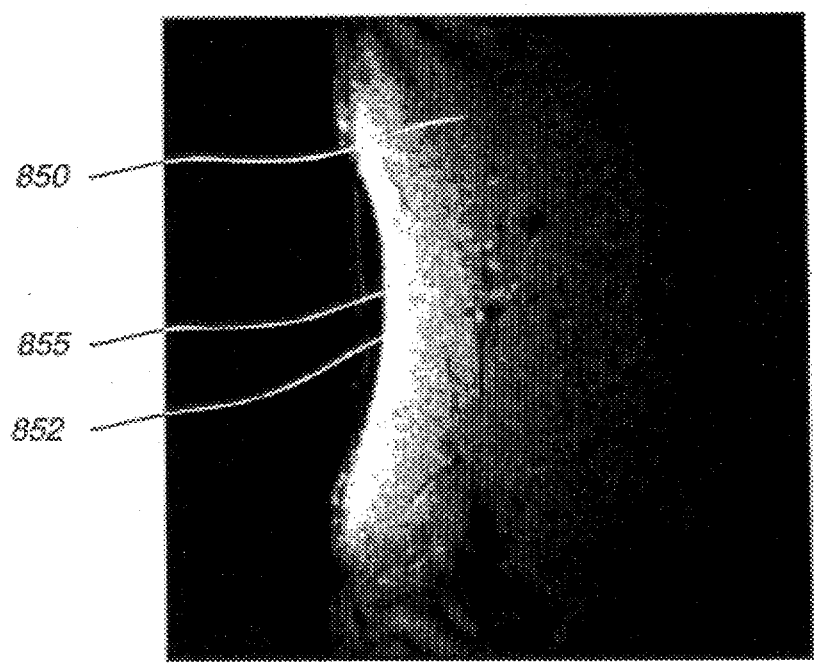
FIG._12B

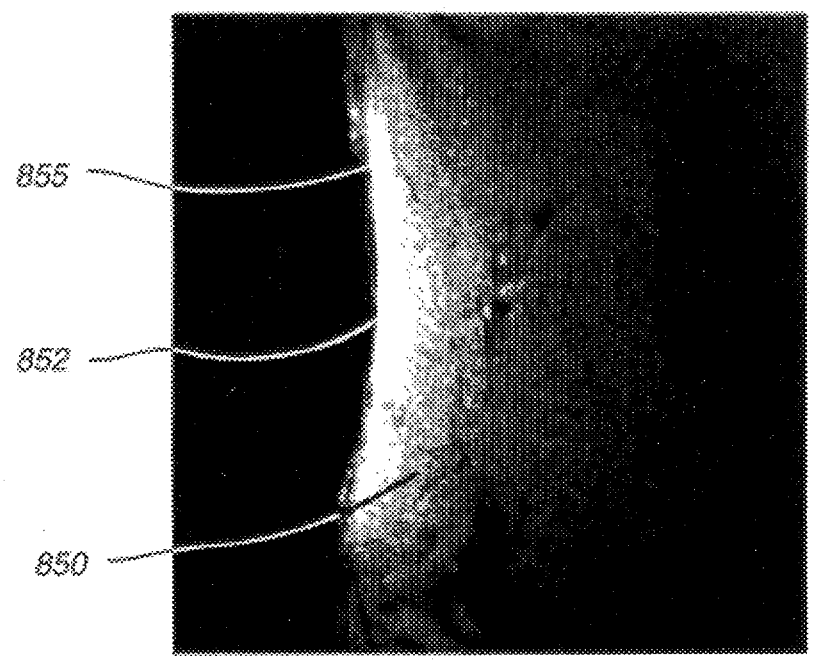
FIG._12C
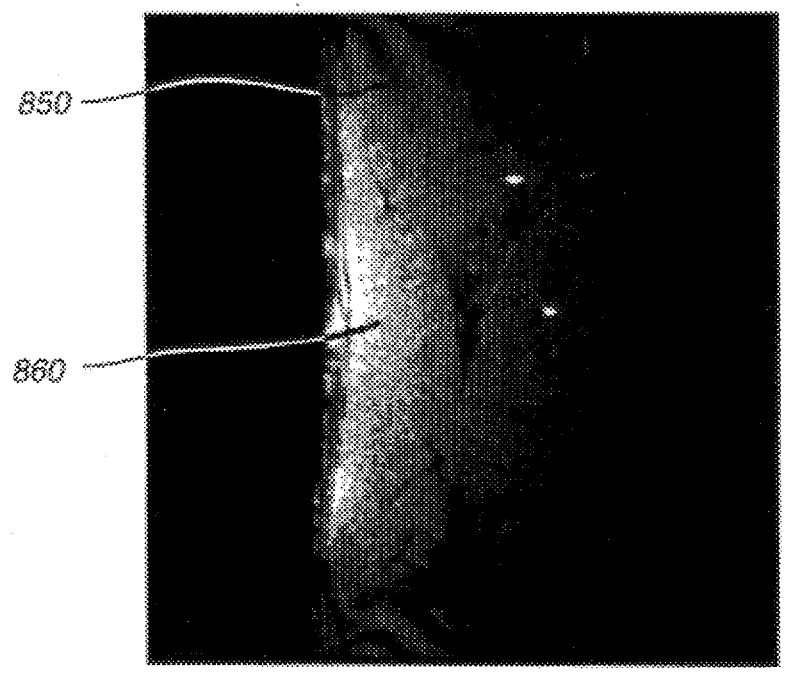
FIG._12D

MAGNETIC RESONANCE IMAGING ASSISTED CRYOSURGERY

This is a divisional of application Ser. No. 08/035,455, now U.S. Pat. No. 5,433,717 filed Mar. 23, 1993.

BACKGROUND OF THE INVENTION

Cryosurgery is a common and effective surgical procedure in which freezing is used to destroy undesirable tissue. The procedure is used in many areas of medicine such as dermatology, gynecology, otolaryngology, proctology, veterinary medicine. In cryosurgery, freezing is usually accomplished by placing a metallic cryosurgical probe, insulated except at its tip, in contact with the subject tissue to be frozen. As the probe is cooled internally (by either circulating a refrigerant (cryogen), Joule Thompson effects, Peltier effects, or by means of heat pipes) heat is removed from the tissue by conduction and a region of frozen tissue grows outward from the probe. When an adequate amount of tissue has been frozen, the flow of cryogen is stopped and the tissue is allowed to thaw.

One of the advantages of cryosurgery is that it can treat tumors focally. Small volumes can be destroyed using a thin needle-like cryosurgical probe, while larger volumes can be destroyed with larger probes or multiple probes. Multiple sites may be treated in this manner and irregularly-shaped volumes can be treated using multiple probes. Retreatment is possible if the disease recurs.

Because tissues can be treated focally, cryosurgery has the potential to spare more adjacent healthy tissue than resection, radiotherapy, or hyperthermia. Another advantage of cryosurgery is that it is easy to control because the freezing process is relatively slow, usually on the order of 1 mm/min. If the therapy is adequately monitored, freezing can be halted before the freezing interface reaches sensitive tissues. An additional advantage of the slow freezing rate of cryosurgery is that capillaries freeze while larger vessels, which act as local heat sources, remain undamaged. Cryosurgery is therefore effective in treating otherwise unresectable solid tumors abutting large blood vessels.

Cryosurgery has also been successfully used in the treatment of many benign and malignant skin cancers. [Torre, D., "Cryosurgery of Basal Cell Carcinoma," *Journal of the American Academy of Dermatology*, 1986; 15(5):917–29. ] [Breitbart] [Kuflik, A., et al., "Lymphocytoma Cutis: A Series of Five Patients Successfully Treated with Cryosurgery," *Journal of the American Academy of Dermatology*, 1992; 26:449–52] [Tappero, J. W., et al., "Cryotherapy for Cutaneous Kaposi's Sarcoma (KS) Associated with Acquired Immune Deficiency Syndrome (AIDS); A Phase II Trial," *Journal of Acquired Immune Deficiency Syndromes*, 1991; 4(9):83946] [Dachow-Siwie'c, Elzbieta, "Treatment of Cryosurgery in the Premalignant and Benign Lesions of the Skin," *Clinics in Dermatology* 1990; 8(1):69–79]. For lesions which are less than 3 mm in depth and benign, the recommended treatment is a liquid nitrogen spray, open or constrained by a neopreme cone barrier or otoscope cone [Torre, D., "Cryosurgery of Basal Cell Carcinoma," *Journal of the American Academy of Dermatology*, 1986; 15(5):917–29.]]. The depth and lateral extent of the cryolesion is estimated by the surgeon to be some percentage of the lateral spread of the frozen region at the surface [Torre, D., "Cryosurgery of Basal Cell Carcinoma," *Journal of the American Academy of Dermatology*, 1986; 15(5):917–29]. However, for tumors which are deeper than 3 mm, or for malignant tumors, some surgeons prefer a closed probe. It is recommended that some type of instrumentation be used during surgery in order to monitor the depth dose. Thermocouple tipped hypodermic needles are the most common method of instrumentation, but ultrasound and electrical resistance/impedance measurements have also been used. Though thermocouple measurements are the most common, they give the surgeon only a rough idea of the zone of cold injury based on one or more discrete measurements. Single point measurements may be an ineffective measure of the depth of the dose due to variations in fat content and thus the local tissue thermal conductivity, increased blood flow in the region near the cryolesion [Bircher, A. J., Buchner, S. A., "Blood Flow Response to Cryosurgery on Basal Cell Carcinomas," *Acta Derm Venereol* (Stockholm) 1991; 71:531–3] or heat sources presented by medium sized blood vessels.

MRI has been shown to be useful in determining skin lesion depths, and is recommended by Zemtsov et. al. for preoperative evaluation of lesions [Zemtsov, A., et al., "Magnetic Resonance Imaging of Cutaneous Neoplasms: Clinicopathologic Correlation," *Journal of Dermatological Surgery and Oncology*, 1991;17:416–22; Zemtsov, A., et al., "Magnetic Resonance Imaging of Cutaneous Melanocytic Lesions," *Journal of Dermatological Surgery and Oncology*, 1989; 15:854–58]. Zemtsov and colleagues have demonstrated that several types of lesions can be successfully imaged using a commercially available General Electric brand 1.5 Tesla NMR spectrometer, and have shown that NMR calculated tumor depths correlate well with Breslow's measured depths.

The idea of using cold in medical therapeutics has been documented as early as the third century BC but its use in treating tumors was first attempted successfully during the last century by James Arnott. Contemporary cryosurgery can be traced to the early 1960's when Cooper and Lee developed a cryosurgical apparatus consisting of a hollow metal tube, vacuum insulated except at its tip, through which liquid nitrogen flowed [Ablin, R. J., *Handbook of Cryosurgery*, Marcel Dekker Inc., New York, 1980]. They treated Parkinsonism by freezing the basal ganglia until the patient's tremor subsided. Although the treatment was effective in providing palliation, it was replaced by drug therapy when L-Dopa became clinically available. During the sixties and early seventies the cryosurgical treatment of skin lesions and lesions of other tissues outside the body provided satisfactory results [Gage, A., "Current Progress in Cryosurgery," *Cryobiology* 25:483–486, 1988. Rubinsky, B., Onik, G., "Cryosurgery: Advances in the Application of Low Temperature to Medicine," *International Journal of Refrigeration*, 14: 1–10, 1991. However, enthusiasm waned for the technique after initial attempts to treat tumors deep in the body. The reasons for the reduction in interest in cryosurgery are due to two problems faced by surgeons:

1) Since the frozen region propagates from the probe into opaque tissue it is impossible to visually monitor the extent of the frozen region. This can result in either insufficient freezing, leaving undesirable tissues unfrozen, or too much freezing which can damage essential tissues.

2) Since freezing itself does not always result in tissue damage, it is difficult to estimate how much of the frozen tissue is actually destroyed.

Understandably, surgeons have been reluctant to use a technique in which they are unable to observe and control the immediate consequences of their actions. However, the latest advances in imaging technology have the potential for overcoming the two problems noted above. In fact, intraoperative ultrasound technology has already facilitated cryosurgery in the liver and prostate with good results [Onik, G., Rubinsky, B., Zemel, R., Weaver, L., Diamond, D., Cobb, C., Porterfield, B., "Ultrasound Guided Hepatic Cryosurgery in the Treatment of Metastatic Colon Carcinoma; Preliminary Results," *Cancer* 67:901–907, 1991. Onik, G., Porterfield, B., Rubinsky, B., Cohen, J., "Percutaneous Transperineal Prostate Cryosurgery Using Transrectal Ultrasound Guidance: Animal Model," *Urology* 37:277–281; 1991.] However, ultrasonic monitoring of cryosurgery which utilized the reflected pressure waves from the freezing interface has drawbacks. First, ultrasound only provides a planar section of the three-dimensional ice front. Second, the region behind the freezing interface (which reflects the pressure waves) is in shadow and cannot be observed. In the liver, this problem can be overcome by moving the ultrasound transducer to a different location to obtain a different point of view. However, imaging of the prostate is only possible from a limited number of sites. Irregular ice structure in the prostate hidden from the ultrasonic monitoring can result in complications such as urethrorectal or urethrocutaneous fistulas. Third, many organs such as the brain are not easily accessible to ultrasound. Fourth, ultrasound shows only the position of the freezing interface, but does not provide information concerning the extent of tissue damage.

Nuclear Magnetic Resonance (NMR) monitoring of cryosurgery can circumvent many of the abovementioned problems. NMR works by putting the sample in a strong static magnetic field, applying a transient magnetic field to the nucleus of atoms in a target region and recording the radio frequency signals emitted as they revert to their unexcited state. The frequency is a function of the atom excited, the positional and orientational relation between the atom and its neighbors in a particular molecule and the local applied field. Therefore the emitted signal can be used to determine the presence of certain atoms and their chemical environment. The intensity of the signal can be correlated to the amount of the investigated species present. Other factors also affect the signal emitted, such as temperature or thermodynamic state. Some of the most important species studied in biological NMR are protons, phosphorous, sodium, and carbon. NMR imaging can be used to monitor freezing during cryosurgery and to optimize the cryosurgical procedure. NMR spectroscopy and spectroscopic imaging can also provide information concerning the relation between tissue that was frozen and tissue that is damaged.

MR imaging (MRI) is a promising tool for assisting cryosurgery for several reasons:

1. Prior to surgery, anatomical information of the region to be frozen can be obtained from MRI and used in cryosurgical treatment planning. The information can be used to model the freezing process and calculate the optimal number of cryoprobes to use, the locations they should be placed at, and the optimal freezing protocol. These procedures can be performed not only with images from MRI but also with images from ultrasound CT, PET and other imaging techniques.

2. Fast, multiple-slice MRI can provide three or more planes acquired in less than 60 seconds, and can provide three-dimensional images of the frozen region during cryosurgery. This provides adequate time resolution to follow the freezing process and to make treatment protocol decisions. MRI imaging can be used to monitor the extent of freezing since ice is invisible under proton NMR while unfrozen tissue is not. The transition of water from liquid to solid is accompanied by large decreases in the proton NMR signal from the water since interactions that are averaged to near zero by molecular tumbling in the liquid (motional narrowing) become significant in the solid thereby increasing relaxation rates by orders of magnitude. This makes water protons in ice invisible to standard NMR imaging techniques and frozen regions appear black [Isoda, H., "Sequential MRI and CT Monitoring in cryosurgery—an experimental study in polyvinyl alcohol gel," Panthom Nippon Igeku Hoshagen Gakkai Zasshi, *Nippon Acta Radiologica*, 49:1096–1001, 1589 (in Japanese). Isoda, H., "Sequential MRI and CT monitoring in cryosurgery—an experimental study in rats," *Nippon Acta Radiologica*, 49:1499–1508, 1989].

The minimum requirement for monitoring cryosurgery is that the position of the freezing interface be ascertainable. Thus almost any NMR imaging method may be employed, including fast and ultra-fast methods such as Fast Low-Flip Angle NMR (FLASH), echo-planar NMR, and radio frequency spoiled gradient echo, i.e. a FLASH sequence with the transverse coherence spoiled by randomizing phase radio frequency pulses. [Cohen, M. S., and Weisskoff, R. H., "Ultra-fast Imaging," *Magnetic Resonance Imaging* 9., 1–37 (1991). Zur, Y., Wood, M., and Neuringer, L., "Spoiling of Transverse Magnetization in Steady State Sequences," *Magnetic Resonance Medicine* 21, 251–263 (1991)].

3. Real-time NMR imaging can provide information on the state of the tissue in and around the freezing interface such as the position of the freezing interface, its velocity, the temperature distribution in the unfrozen region, and the temperature distribution in the unfrozen region. The temperature distribution in the unfrozen region can be found, for example, from T1-weighted Inversion Recovery Rapid Acquisition with Relaxation Enhancement (IR-RARE) sequences [Dickinson, R. J., Hall, A. S., Hind, A. J., Young, I. R., "Measurement of Changes in Tissue Temperature using MR Imaging," *Journal of Computer Assisted Tomography*, 1986:10; 468–472], and other techniques [Le Bihan, D., Delannoy, J., Levin, R. L., "Temperature Mapping with MR imaging of Molecular Diffusion: Application to Hyperthermia," *Radiology* 1589:853–857], and [Rubinsky, B., Gilbert, J. C., Onik, G. M., Roos, M. S., Wong, S. T. S., Brennan, K. M., "Monitoring Cryosurgery in the Brain and in the Prostate with Proton NMR," *Cryobiology, April* 1993], and the temperature distribution in the frozen region can be calculated knowing the position of the interface and the temperature of the probe as was done with ultrasound [Gilbert, J. C., Rubinsky, B., Onik, G. M., "Solid-Liquid Interface Monitoring with Ultrasound During Cryosurgery," ASME paper #85-WA/HT-83, 1985]. This information can be used to adjust and control the freezing process in situ, either by providing information to the surgeon or in an automated control system.

4. Post-cryosurgical MR follow-up provides a noninvasive means of determining the efficacy of treatment. T2-weighted MRI can track the evolution of edema and other changes in and around the tissue treated with cryosurgery over periods of minutes to days [Vining, E., Duckwier, G., Udkoft, R., Rand, R., Lufkin, K., "Magnetic Resonance Imaging of the Thalamus Following Cryothalamotomy for Parkinson's Disease and Dystonia," *Journal of Neuroimaging*, 1, 196–198 (1991); Rubinsky, B., Gilbert, J. C., Onik, G. M., Roos, M. S., Wong, S. T. S., Brennan, K. M., "Monitoring Cryosurgery in the Brain and in the Prostate with Proton NMR," in print, *Cryobiology*, 1993]. T1-weighted MRI can detect bleeding and changes in the state of any post-cryosurgical hemorrhage. With the use of contrast agents such as Gd-DTPA (gadopentetate dimeglumine), T1-weighted MRI can also delineate the region of blood-brain barrier disruption after freezing as will be discussed below. Furthermore, spectroscopy and spectroscopic imaging of phosphorous, carbon, and sodium are also useful in determining the extent of tissue damage after cryosurgery. In the case of sodium, it is the ratio between the intracellular to extracellular sodium which are indicative of damage. In the case of phosphorous, it is the molecular composition, and the relative composition in which the compound appears as, ATP, ADP, phosphocreatine or inorganic phosphorous which indicates the extent of the damage.

In summary, NMR imaging can be used in four different stages during cryosurgery to improve the results of the procedure: 1) in the preoperative stage in a predictive mode to plan the procedure and optimize the application of cryosurgery; 2) during cryosurgery to image the process of freezing; 3) for interactive control during the surgery to control and optimize the application of cryosurgery; and 4) in the post-operative stage to evaluate the damage induced by the procedure.

Despite the advantages of MRI, the efficient use of MRI with cryosurgery is inhibited by the nature of the MRI apparatus and limitations of the technique. In particular:

1) MRI operates in a magnetic environment and employs radio frequency electromagnetic energy. Consequently conventional metallic cryosurgical probes cannot be used with MRI. Experiments reported by other groups were limited to the use of a gauze immersed in liquid nitrogen and then applied to the skin [Isoda, H., "Sequential MRI and CT Monitoring in Cryosurgery— an Experimental Study in Rats," *Nippon Acta Radiologica*, 49:1499–1508, 1989 (in Japanese)], or to the use of a styrofoam cup filled with liquid nitrogen [Matsumoto, R., Oshio, K., Jolesz, F., "Monitoring of Laser and Freezing Induced Ablation in the Liver with T1—Weighted MR Imaging," *Journal of Magnetic Resonance Imaging*, 2, 555–562, 1992]. The present invention relates to the design of a cryosurgical probe compatible with MRI.

2) It is preferable for MR imaging that the region imaged be stationary with respect to the magnet. The present invention is therefore a stereotactic apparatus for positioning cryosurgical probes in relation to the MRI apparatus.

3) During cryosurgery the region of interest that is frozen and imaged is usually small relative to the whole region imaged by MRI. This is particularly the case in dermatology where freezing penetrates only a few millimeters from the probe. The present invention is therefore directed to a cryosurgical probe on which the radio frequency coil of the MRI system is attached. This generates a much higher signal to noise ratio in the region of interest, with a much higher resolution (of about 100 µm). This is an optimal solution, since the cryosurgical probe is naturally in the center of the region of interest. Another advantage of mounting the coil on the probe is that it is then possible to construct a probe where the cryogen also cools the coils, thereby reducing thermal noise and increasing the signal-to-noise ratio still further.

4) The low signal intensity of atomic species other than protons makes the signal-to-noise ratio of these species (such as phosphorus or sodium) very low. Attaching a receiver coil tuned to these species to the cryosurgical probe is advantageous since the signal/noise ratio is significantly improved by analyzing only the area of interest. Furthermore the cryosurgical probe is by the nature of its function in the center of the region of interest.

Attaching the MR receiving coil to the cryosurgical probe provides the advantages of increased resolution in the area of interest during cryosurgery, and increased ability to determine the effectiveness of cryosurgery, without the need for introducing additional devices in the patient. Such an arrangement may also be useful with other microsurgical techniques, such as laser surgery, or mechanical resection.

The advantage of an MRI assisted microsurgical system is that it can provide a better resolution in the region treated by various surgical techniques and it can be used to better monitor tissues during surgery. Furthermore, since it involves only the attachment of small electric components to the surgical device, it does not substantially increase the bulk of the device. This technique can remove the need for optical imaging of surgical procedures using fiber optics, thereby facilitating surgery with smaller devices and in smaller areas.

The present invention relates generally to methods and apparatus for improving the results of cryosurgery, and more particularly to methods and apparatus for improving the results of cryosurgery using preoperative surgical optimization planning, real-time NMR imaging during surgery, control of the cryosurgical procedure using NMR image information, and/or post-operative NMR monitoring of cryodamage.

An object of the present invention is to provide methods and apparatus for improving cryosurgical results.

Another object of the present invention is to provide methods and apparatus for improving cryosurgical results using preoperative surgical planning in combination with MR image information.

Another object of the present invention is to provide methods and apparatus for improving surgical results, particularly cryosurgical results, using real-time NMR imaging during surgery.

Another object of the present invention is to provide methods and apparatus for improving cryosurgical results by controlling the cryosurgical procedure using real-time NMR image information.

Another object of the present invention is to provide methods and apparatus for postoperative NMR monitoring of cryodamage.

Another object of the present invention is to provide methods and apparatus for utilizing the heat and mass transfer equations in the preoperative planning stage and during surgery to improve cryosurgical results.

Another object of the present invention is to provide methods and apparatus for determining tissue temperatures using NMR data to improve cryosurgical results.

Another object of the present invention is to provide methods and apparatus for determining tissue temperatures by solving the heat and mass transfer equations in the frozen region.

Another object of the present invention is to provide methods and apparatus for improving cryosurgical results using an MR compatible cryoprobe and stereotactic device.

Another object of the present invention is to provide methods and apparatus for improving cryosurgical results by increasing the resolution of MR monitoring using an MR coil mounted on the cryoprobe.

Another object of the present invention is to provide methods and apparatus for evaluating cryosurgical results using NMR spectroscopy and imaging, such as phosphorous-31 or sodium-23 spectroscopy and imaging.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to methods and apparatus for real-time interactive cryosurgery utilizing information obtained from magnetic resonance imaging.

The present invention is directed to a stereotactic system for magnetic resonance monitoring of cryosurgery which includes a frame which is transparent to magnetic resonance imaging, a cryoprobe compatible with MRI, a means for positioning the cryoprobe relative to the frame, and a reference object such as a magnetic resonance visible marker for orientation and positioning purposes.

The present invention is also directed to methods for monitoring damage to a biological tissue using sodium-23 spectroscopic imaging, or phosphorus-31 spectroscopic imaging and detecting changes in PCr, inorganic phosphorous, or ATP levels.

The present invention is also directed to a cryoprobe which has a radio frequency magnetic resonance coil mounted at the intracorporeal end thereof, thereby providing an increased signal-to-noise ratio.

The present invention is also directed to a method for monitoring temperatures of a freezing region in a biological tissue with proton magnetic resonance imaging. The method consists of correlating the region which generates no proton resonance signal with the frozen part of the freezing region, solving the heat equation in the frozen part utilizing the known temperatures at the boundaries, and determining temperatures in the unfrozen part by calculations based on measured T1 times.

BRIEF DESCRIPTION OF THE DRAWING

The accompanying drawings, which are incorporated in and constitute a part of the specification, schematically illustrate a preferred embodiment of the invention and, together with the general description given above and the detailed description of the preferred embodiment given below, serve to explain the principles of the invention.

FIG. 1 shows an embodiment of the stereotactic cryosurgical probe system of the present invention.

FIG. 2 is a cut-away view of the stereotactic probe system of FIG. 1 in the bore of an magnetic resonance imaging magnet.

FIGS. 3a–e show view of a rabbit brain prior to (a), during (b and c) and after cryosurgery (d and e). FIG. 3f shows a histological section of the brain for comparison.

FIGS. 4a, 4b and 4c show cross-sectional, magnified, and end views, respectively, of a surface cryoprobe according to the present invention.

FIGS. 5a and 5b show the circuitry of the proton and spectroscopy coils, respectively, of the surface cryoprobe shown in FIGS. 4a, 4b and 4c.

FIGS. 6a and 6b show cross-sectional side and end views, respectively, of a prostate cryosurgical probe according to the present invention.

FIGS. 7a shows a magnetic resonance image of the abdomen of a dog. The prostate, visible in the central square in FIG. 7a, is shown magnified in FIGS. 7b through 7g during freezing and thawing of a lobe of the prostate.

FIG. 8a shows a histological section of the prostate shown in FIGS. 7a–7g. FIG. 8b is a magnified view of the boundary of the cryolesion.

FIG. 9 provides experimental data correlating magnetic resonance signal intensity versus temperature.

FIG. 10a plots signal intensity versus position at two times during the propagation of a freezing interface across a sample.

FIG. 10b shows a comparison between theoretical and experimental data of temperature versus position in the unfrozen region during freezing.

FIGS. 11a through 11r show a time sequence of images of a freezing interface propagating through a gel taken with a surface cryoprobe of the present invention.

FIGS. 12a through 12d show a time sequence of images of a cryolesion on a rabbit leg taken with a surface cryoprobe of the present invention.

DESCRIPTION OF THE PREFERRED EMBODIMENTS

The present invention will be described in terms of the preferred embodiment. The preferred embodiment is an apparatus and method for magnetic resonance imaging assisted cryosurgery.

One of the major problems faced by cryosurgeons is the inability to evaluate the effectiveness of the treatment immediately. However, NMR provides the ability to perform such evaluation through phosphorous-31 ($^{31}P$) and sodium-23 ($^{23}Na$) spectroscopic imaging to asses cell damage produced by freezing. Although other nuclei can be also seen with NMR and may be also useful for monitoring damage, sodium-23 and phosphorous-31 are physiologically significant and because of their natural abundance they are easily detected by NMR. Spatial resolution in spectroscopic imaging experiments can be on the order of 1 cm for $^{31}P$, and 0.5 cm for $^{23}Na$, for a signal-to-noise ratio of 10 in a 30 min acquisition time. Spectra acquired with implanted receiver coils or with coils on the cryosurgical probe require substantially reduced acquisition times.

The following changes are observed in tissue following thawing:

1) A decrease in PCr (phosphocreative) and ATP (adenosine triphosphate) and increase in inorganic phosphorous (Pi) lines in proportion to the fraction of damaged cells.

2) An increase in the total $^{23}Na$ signal due to cell membrane disruption and edema, since the amount of intracellular sodium is less than that of extracellular sodium. If the cell membrane is broken, sodium brought by the blood supply can also fill the space occupied by the cells. The changes in the $^{23}Na$ signal are most easily observed in the brain because of the small size of the extracellular volume in normal tissue (where the $^{23}Na$ concentration is high.)

Preoperative planning

Conventionally, cryosurgery is performed using a single cryosurgical probe. The surgeon would introduce the probe in the approximate center of the tissue to be destroyed and the freezing would proceed until, to the best estimate of the surgeon, the tumor or tissue to be destroyed has been frozen completely.

The ability to image the process of freezing in real time using various means such as ultrasound, has resulted in more precision and the application of cryosurgery to more complex situations. Irregularly shaped tissues, such as the prostate, can be frozen using multiple cryosurgical probes to achieve an irregularly shaped frozen region. During a typical cryosurgical procedure performed with imaging, the probes can be placed accurately by the surgeon and the extent of the frozen region can be monitored accurately.

Despite the fact that the probes can be accurately placed and the extent of freezing can be observed, the criteria for the actual probe placement has not changed since the pre-imaging period. The placement of the probes is still informed by experience and based on an estimate of how the freezing interface will develop. While in the past lack of accuracy in placement and in freezing would not affect the overall results of this procedure, which was inaccurate by itself, with imaging the placement of the probes becomes one of the main sources of inaccuracy in cryosurgical treatment. The probes must be accurately placed prior to freezing since once the freezing process has begun it is impossible to remove the probes from the tissues.

Pretreatment planning is important since it can provide the cryosurgeon with valuable information on the placement of multiple cryosurgical probes, and the design of freezing protocols. Multiple cryoprobes are useful for freezing several sites simultaneously, regions too large to be frozen by a single cryoprobe, or unusually shaped regions. Generally, surgeons have difficulty in planning surgical procedures using multiple probes because of the large number of variables that must be calculated simultaneously. Providing the surgeon with an estimate of the performance of a particular cryosurgical protocol in the planning stage, will allow pretreatment evaluation of alternate plans. Treatment planning is also important because cryosurgical probes may not be moved once freezing starts. Thawing, repositioning the probes, and refreezing after thawing is time-consuming, so it is important to achieve the most tissue destruction in the target region with a minimum of freezing episodes.

In the pretreatment planning stage, anatomical information of the target region in a specific tissue obtained from NMR images or other imaging techniques is incorporated into the mathematical model to provide guidelines for selecting the number of cryosurgical probes, and the types, sizes, placement, and paths of introduction of the probes. Planning a cryosurgical procedure involves the following steps:

1) Identifying a target region to be frozen, and any adjacent critical anatomy that must be protected from freezing.
2) Estimating the heat transfer properties of the tissue, based on factors such as the thermal conductivity of the tissue and the locations of any local heat sources such as blood vessels.
3) Running an optimization program to determine the number, type, and size of the cryosurgical probes, together with the optimal path of insertion and the required thermal protocol.

Identification of the target region is accomplished using multi-slice or three-dimensional NMR datasets much as it is done in radiotherapy. The imaging technique is selected to yield good tissue contrast between the tumor to be treated and the surrounding tissue. For instance, multi-slice spin echo (TE=33/100 ms, TR=2000 ms) or 3-D spoiled sequences are preferred techniques for gathering anatomical information. In each slice, the target region is identified by automated or manual region drawing, and the bounding surface constructed by tiling between slices. In addition, any thermally or structurally important structures are identified as regions of interest. Coordinates of all significant structure in the target region and vicinity and is stored in the computer together with the relevant thermal properties of the tissue for use in developing the treatment plan. A velocity compensated three-dimensional FLASH technique is employed in which blood flowing into the region appears bright. Slabs of three-dimensional slices are oriented to obtain maximum contrast from inflowing blood. Vessels are identified by adjusting the contrast for maximum visibility (thresholding), and a vascular tree for the volume of interest is stored in the computer. Because we consider small volumes with only a few large vessels, tracking vessels from slice to slice is not difficult and may be done by hand if necessary. The vasculature in the target volume is used in the heat transfer model.

After the region to be treated and the surrounding tissues are culled by NMR, the thermal characteristics of the tissues are identified from a tissue library. The region to be destroyed is identified together with inadmissible paths for probe penetration and other operation constraints. Then, the optimization program is run to provide the surgeons with the required information concerning the number and types of probes, the path of insertion, and the required temperature on the cryosurgical probes. This technique using a downhill simplex optimization procedure is described in detail in Keanini, R., Rubinsky, B., "Simulation and Optimization of Three- Dimensional Multi-Probe Prostatic Cryosurgery," *J. Heat Transfer*—ASME Trans, 114, 796–801, 1992, and is incorporated herein by reference.

Stereotactic cryosurgery system

Despite the obvious advantages of using NMR with cryosurgery there are also drawbacks. In particular, access into an NMR apparatus is limited. Therefore, NMR monitoring of cryosurgery requires special preparations. The stereotactic apparatus of the present invention facilitates positioning of the cryosurgical probes within the tissue, relative to the NMR device and the patient. The device must be made mostly with materials that do not disrupt NMR signals, but must also contain some materials such as reference objects that are visible with NMR when those materials are located at known positions relative to the cryosurgical probe(s). For example, fastening devices for the probes can be marked with material visible under NMR. The device must also contain a means of attachment to the patient at known positions and to the NMR apparatus at predetermined positions. In a typical procedure the probe positioning device is attached to the patient and positioned at a predetermined position within the NMR magnet so that the tissue to be treated is optimally visible with NMR and the specific NMR visible sites on the attachment device are also visible under NMR monitoring. The path is evaluated either by the surgeon or using the preplanning computer programs described earlier. If needed, the positioning device is moved relative to the patient and the NMR machine until an optimal path can be achieved.

An embodiment of the magnetic resonance imaging compatible stereotactic holder 300 of the present invention is shown in FIG. 1. The stereotactic holder 300 is particularly adapted for holding a small mammal, such as a rabbit, for cryosurgery of the brain. Other embodiments suited for cryosurgery of other body parts of other animals may also be constructed and are also within the scope of the present invention. The stereotactic holder 300 is constructed from clear plexiglass plates having thicknesses of ¼ and ³⁄₁₆ inches, and nylon screws. Most nylon screws which secure the plexiglass plates are omitted from FIG. 1 for clarity. No metal parts are used in the construction of the stereotactic holder 300.

The holder 300 consists of a positioning plate 310, and an operations section 320 attached to the positioning plate 310. Left and right calibration scales 312l and 312r are provided along the side edges of the positioning plate 310 for the purpose of gauging the longitudinal location of the holder 300 inside the magnet 400, as shown in FIG. 2. The positioning plate 310 has a width of approximately 21 cm. The operations section 320 has a base plate 325 with left and right flanged edges 327l and 327r, respectively. (Components of the same type positioned on the left and right sides of the stereotactic holder 300 will be given reference numerals appended with the letters "l" and "r" to denote the left and right components, respectively. Similarly, front and back components of the same type will be given reference numerals appended with the letters "f" and "b", respectively. When left and right, and/or front and back components are referred to collectively, the reference numeral will not be appended with a letter.) The base plate 325 has a width of approximately 10 cm.

Attached to the flanged edges 327l and 327r adjacent the positioning plate 310 are left and right shoulder plates 330l and 330r, respectively. Attached to the flanged edges 327l and 327r adjacent the shoulder plates 330 are left and right positioning plates 340l and 340r, respectively. The shoulder plates 330 and the positioning plates 340 have a height of approximately 8 cm. The right adjustment plate 340r has a front vertical slot 345rf and a rear vertical slot 345rb. Similarly, left adjustment plate 340l has two vertical slots 345l. A U-shaped probe bracket 350 is mounted on top of the adjustment plates 340 by four pairs of nylon adjustment screws 355, one pair extending through each vertical slot 345 to screw holes (not shown) in the bracket 350. By screwing the adjustment screws 355 into the probe bracket 350, the force between the heads of the adjustment screws 355, the adjustment plates 340, and the vertical sections of the probe bracket 350 immobilizes the probe bracket. A stereotactic holder probe 370 is mounted in the midsection of the probe bracket 350.

As shown in FIG. 1, and the cross-sectional view of FIG. 2, a liquid nitrogen inlet tube 372 and a liquid nitrogen outlet tube 374 extend from the body 376 of the probe 370. The inlet tube 372 and the outlet tube 374 are mounted 60° apart, as shown in FIG. 1. (The inlet and outlet tubes 372 and 374 are shown mounted 180° apart in FIG. 2 for clarity.) The inlet tube 372 is L-shaped. The inlet and outlet tubes 372 and 374 are mounted on the body 376 near the upper end of the body 376 so that there is clearance between the upper end of the body 376 and the magnet bore while still maintaining structural integrity. The body 376 is approximately 4 cm high, and has a width of approximately 1.5 cm. The body 376 of the probe 370, and the inlet and outlet tubes 372 and 374 are made of Pyrex glass. The lower section of the probe 370 is a conical section, the lower tip being circular with a width of approximately 0.7 cm.

The inlet tube 372 is connected via silicone rubber tubing (not shown) to a liquid nitrogen dewar (not shown). The flow rate of the liquid nitrogen is monitored by observing the state of the nitrogen leaving the exhaust outlet 374. When the exhaust is in the liquid state the flow rate is greater than necessary to produce the minimum possible temperature at the tip of the probe 370. The bottom end of the inlet tube 372 is adjacent the bottom of the probe body 376 (approximately 0.6 cm above the bottom surface) so that the liquid is delivered directly to the tip of the probe 370. The exhaust outlet 374 is also connected to silicone rubber tubing (not shown) to channel the exhaust gases away from the subject so as not to cause cooling or freezing of regions of the subject other than those in direct contact with the tip of the probe 370.

FIG. 2 is a front view of the stereotactic holder 300 positioned inside the cylindrical interior cavity 410 of a magnet 400 such as the Bruker 2.35 Tesla magnet owned by Lawrence Berkeley Laboratories, combined with a cut-away view of the probe 370. The positioning plate 310 has a known width, and therefore the height of the components of the holder 300, such as the probe 500 and the head screws 360, are also known. The width of the positioning plate 310 is chosen such that the holder 300 is optimally positioned to minimize gradients in the magnetic field generated by the magnet 400. The graduations of the calibration scale 312 along the side edge of positioning plate 310 provide a measurement of the distance between the probe 370 and the end of the magnet 400. The position of the probe 370 along the longitudinal axis of the cavity 410 is determined by noting the numerical value of the first graduation which extends past the end of the magnet 400.

To use the stereotactic holder 300 for MRI assisted cryosurgery of a rabbit, the rabbit (not shown) is placed supine on the holder 300 with its head positioned between the head screws 360, its shoulders between shoulder plates 330, and its rear quarters resting on the positioning plate 310. The position of the head is stabilized by adjusting head screws 360 so as to produce a light pressure on the skull. The cryoprobe 370 is brought into contact with the surgical area by vertical adjustment of the probe bracket 350. The cryoprobe 370 is repositioned by loosening the adjustment screws 355, positioning the bracket 350, and retightening the adjustment screws 355.

Cryosurgical experiments were performed on an adult New Zealand rabbit weighing 3–4 kg. The experiments were conducted under approved LBL Animal Welfare Research Committee protocols. These experiments are described in detail in Gilbert, J. C., Rubinsky, B., Roos, M. S., Wong, S. T. S., and Brennan, K. M., "MRI-Monitored Cryosurgery in the Rabbit Brain," *Magnetic Resonance Imaging*, submitted January 1993, and is incorporated herein by reference. The rabbit was anesthetized with an I.M. (intra muscular) injection of ketamine (30 mg/kg), rompun (3 mg/kg), and acepromazine (0.6 mg/kg), and additional doses of anesthesia were administered as necessary by I.M. The rabbit was immobilized in the stereotactic holder 300 with the cryoprobe 370 held against the skull, approximately 1 cm caudally from the eye sockets over the central portion of the cerebral cortex. The entire rabbit/cryoprobe/frame assembly was then placed in the magnet bore 410 with the brain located in the center of the magnet 400. Sagittal scout images were acquired (spin-echo; TE=33 ms; TR=400 ms) with a drop of water in the tip of a Pyrex cryoprobe 370 to determine the appropriate freezing location, in this case being the midline center of the surface of the cerebral cortex. The assembly was then removed from the magnet bore 410, the cryoprobe 370 was removed, and a 5 mm diameter hole was made in the skull the appropriate distance from the aforementioned drop of water using a dentist's drill, taking care not to breech the dura. The cryoprobe 370 was replaced in the holder 300 with the tip just touching the surface of the brain. The rabbit/cryoprobe/frame assembly was then put back in the magnet bore in the same location as before. FIG. 3a shows an MRI view of the rabbit brain prior to freezing. The aperture 705 in the skull 700 is visible. The probe 370 is located in the aperture 705 but is not visible since it is constructed of materials transparent to proton NMR.

Baseline images were acquired before freezing in six coronal planes (3 mm thick, 1 mm apart) covering most of the volume of the brain. Because pulse sequences for monitoring freezing were continued throughout the rabbit experiments, baseline images were acquired using several pulse sequences. In particular the pulse sequences were: spin-echo (TE=33/100 ms; TR=2 sec; total acquisition time 12.8 min); T1-weighted spin-echo (TE=28 ms; TR=400 ms; total acquisition time 2.5 min); and radio frequency spoiled gradient echo (TE=14 ms; TR=50 ms; total acquisition time 14 seconds/slice). Radio frequency spoiled gradient echo pulse sequences (TE=14 ms; TR=50 ms) with and without Gd-DTPA is the preferred pulse sequence since it provides good time resolution with adequate signal to noise ratio. T1-weighted spin echo sequences have also been used.

The total acquisition time for an image using radio frequency spoiled gradient echo pulse sequence can be less than 15 seconds. Total time for processing and display is less than 5 seconds under typical network and machine loads. Thus 20 seconds is required to acquire and reconstruct the first slice, and subsequent slices appear every 15 seconds.

Imaging began simultaneously with the opening of the valve on a liquid nitrogen dewar and continued throughout the freeze/thaw cycle. Freezing was conducted for approximately 10 minutes until a freezing interface 710 had progressed approximately 5 mm ventrally into the cerebral cortex as shown in FIG. 3b. This usually occurred after approximately 5 minutes of freezing. Thawing was usually complete within eight minutes after the flow of liquid nitrogen was stopped. After thawing was complete, images were acquired for up to an additional four hours.

Before freezing the rabbit brain appeared normal and major anatomical structures, such as the cerebral cortex, hippocampus, and thalamus, are visible in the spin-echo images. Although less anatomical detail is available from the radio frequency spoiled gradient echo images, these images have adequate spatial resolution and superior time resolution for locating the position of the freezing interface. As shown in FIGS. 3b and 3c, during freezing the boundary 710 between the frozen and unfrozen tissue is a clearly visible circular arc. The dark region 715 in FIG. 3c corresponds to the semicircular section of the bilateral frozen lesion encompassing the cingulate cortex and part of the hippocampus.

In the preferred postcryosurgical follow-up the rabbit is imaged periodically for up to four hours after freezing using spin-echo pulse sequences (TE=33/100 ms; TR=2s) without Gadolinium DTPA. As shown in FIG. 3d, five minutes after thawing is complete the previously frozen region is again visible. There are some contrast changes observable in the region of necrosis. For instance, the development of edema over the four-hour follow-up period is visible using T2-weighted spin-echo imaging. As shown in FIG. 3e, during this period a bright ring 720 corresponding to the freezing boundary is observed to increase in signal intensity. (In FIG. 3e the outline 725 of the probe 370 is also visible due to condensation on its outer surface.) However, the central portion of the lesion is darker than the boundary 720, probably because there is greater destruction of the vasculature there.

The brain section shown in FIG. 3f is a coronal slice through the dorsomedial nucleus of the thalamus. There is good correlation between the right side of the coronal brain section and the NMR images acquired during the experimental procedure. The coronal section is embedded in paraffin, sectioned and stained with hematoxylin and eosin using standard histologic techniques. Grossly, the brain has a roughly circular, symmetrical 17 mm (diameter) reddish brown hemorrhagic and necrotic area in the superficial dorsal cerebral cortex 726 that matches the area of the freezing lesion. This lesion is a pale, edematous oval area symmetric about the cingulate gyrus 727, 17 mm in diameter at the superior surface and extending 7 mm ventrally near to the dorsal surface of the thalamus. The central part of the lesion is hemorrhagic.

The lesion and its T2-weighted NMR image can be seen to correspond closely. These results indicate that NMR imaging may be an accurate estimator of damage in postcryosurgical follow-up in addition to its role in monitoring the freezing process during cryosurgery.

The Surface Probe

Using conventional NMR monitoring techniques the images of larger organs such as the brain provide adequate resolution. The image of smaller organs, such as the skin, the prostate, or the blood vessels, will however suffer from poorer resolution. However, during cryosurgery of the skin or the prostate, a view of the whole body is not of interest, whereas better details of the prostate are highly desirable. During MR imaging, the radio frequency coil usually surrounds the whole body and receives signal from the whole body, while the region of interest is only in the near vicinity of the surgical probe. Therefore, if RF coils are located only in the vicinity of the region of interest, the resolution of the MR image is much better since the signal to noise ratio is higher. If one images the whole body, but is interested only in details in a small portion of the body (the signal), the noise is still generated from the whole area imaged (the body) and the signal to noise ratio is poor. Conversely, if the RF coil images only the region in which surgery is performed, then the signal and the noise come from roughly the same area, and the resolution becomes much better. This is particularly important with low intensity signals, such as those from $^{13}C$, $^{23}Na$, and $^{31}P$. In the present invention the surgical probe itself serves as a chassis on which the RF coils are mounted.

An RF coil acts as an antenna which picks up radio frequency signals. The coil is part of an electrical circuit designed to resonate in the range of frequencies of interest. The coil may have a variety of configurations such as, but not limited, to surface coils, Helmholz coils and solenoid coils [Hurst, G. G., Hua Jiannin, Duerk, J. L., Cohen, A. M., Intravascular (Catheter) NMR Receiver Probe: Preliminary Design Analysis and Application to Canine Iliofemoral Imaging," *Magnetic Resonance in Medicine* 24, 343–357 (1992); Zemtsov, A., et al., "Magnetic Resonance Imaging of Cutaneous Neoplasms: Clinicopathologic Correlation," *Journal of Dermatological Surgery and Oncology*, 1991; 17:416–22; Zemtsov, A., et al., "Magnetic Resonance Imaging of Cutaneous Melanocytic Lesions," *Journal of Dermatological Surgery and Oncology*, 1989; 15:854–58].

The surface probe 500 of the present invention having integrated RF coil is shown in cross-section in FIG. 4a. The probe 500 is comprised of a cylindrical body 510 made of cast acrylic. The body 510 has a central cylindrical boiling chamber 520, and a delivery passage 525 and four exit passages 530 extending from the boiling chamber 520 to the rear of the body 510. As can be seen in the rear view of the probe 500 of FIG. 4c, the four exit passages 530 are evenly spaced around the delivery passage 525. The end of the boiling chamber 520 opposite the delivery passage 525, henceforth to be termed the front end, is sealed with a cylindrical piece of quartz 540, and there are three thin circular pieces of boron nitride loaded silicone 545b, 545c and 545f (referred to collectively by reference numeral 545) in contact with the front face of the quartz 540, as shown in the magnified view of FIG. 4b. Located between the central silicone disk 545c and front silicone disk 545f is a first spectroscopy coil 555a, and located between the central silicone disk 545c and the rear silicone disk 545b is a second spectroscopy coil 555b. The two coils 555 are electrically connected to provide a double coil configuration. The spectroscopy coils 555a and 555b are made of 0.005 inch thick copper foil, and have a diameter of 0.6 inches and a width of 0.1 inch. The quartz 540, silicone disks 545, and coils 555 are held in place by an acrylic cap 560 which is secured to the acrylic body 510 by four nylon screws 565 which are evenly spaced about the perimeter. The quartz 540 is thermally insulated from the acrylic body 510 by a polystyrene insulation layer 562.

A single turn proton coil 535 is mounted to a coil mount 570 which laterally extends from the outside of the acrylic body 510. The proton coil 535 has an outer diameter of 2.8 inches, an inner diameter of 1.8 inches, and is made of 0.005 inch thick copper foil.

The circuitry of the probe 500 is shown in FIGS. 5a and 5b. As shown in FIG. 5a, the proton coil 535 is connected in series to a capacitor C3 having a capacitance of 36 pf and an inductor L2 having an inductance of 45 nH. The series combination of the proton coil 535, the capacitor C3, and the inductor L2 are connected in parallel to a capacitor C1 having a capacitance of 152 pf, and a tunable capacitor C2. The input to this system is grounded on one side and connected to a tunable capacitor C4 on the other side.

As shown in FIG. 5b, the spectroscopy coil 555 is connected in parallel to a capacitor C7 having a capacitance of 91 pf and a tunable capacitor C6. One side of this circuitry is connected to ground and the other side is connected to a tunable capacitor C5. The spectroscopy coil circuitry is tunable to the magnetic resonance frequencies phosphorous-31 or sodium-23. By changing the value of C7, the spectroscopy coil circuit may be also tunable for $^{13}$C or $^{23}$Na nuclei.

The cryoprobe 500 is designed to achieve a uniform temperature profile across the probe surface near the specimen, and to provide optimal imaging. A uniform radial temperature distribution is desired so that the freeze zone in the specimen has a flat ice front in the region to be investigated. The effective thermal resistance between the boiling chamber 520 and the front probe surface is kept low in order to attain high freeze rates. The probe 500 is designed to give a high signal-to-noise ratio, and to pick up FID's, free induction delays or just NMR signals, from a relatively well defined geometric area. Clearly, all construction materials must be suitable for use in a high magnetic field, and are preferably electrically nonconductive.

Uneven liquid nitrogen boiling over a surface such as the front of the boiling chamber 520 creates high thermal gradients on the boiling surface. The quartz 540 at the front of the chamber, together with the polystyrene insulation 562 located between the quartz 540 and the acrylic body 510 provide a system which has a uniform and large thermal gradient only in the axial direction across the quartz 540 and silicone 545. The boron nitride loaded silicone 545 provides a high thermal conductivity matrix for the spectroscopy coil 555. Furthermore, under pressure, the boron nitride loaded silicone 545 offers low thermal contact resistance between both the quartz 520 and the acrylic body encasement 510, lowering the overall thermal resistance of the device in the axial direction.

The probe 500 is constructed such that contact pressure between the quartz 540 and the silicone 545, and between the silicone 545 and the outer encasement 510 is increased as the probe 500 cools. Since the coefficient of thermal expansion of the acrylic body 510 is much larger than that of the quartz 540, cooling of the entire probe 500 causes the silicone 545 to be squeezed slightly. This pressure is required to ensure a consistent total thermal resistance throughout the cooling period.

It is well known that the region for which a surface coil is effective as a probe extends approximately one surface coil radius away from the plane of the coil. There is no definite cut-off and the extent of the region may be altered to some degree by control of the pulse widths, but to first order the range of a coil is set by the effective magnetic field. Thus, with no special encoding the probe 500 will receive signals from a region roughly approximated by a hemisphere whose great circle lies on the coil plane 555 or 535. Surface coils are especially useful for spectroscopy studies of tissue near a surface because the signal-to-noise ratio is high because of the highly localized magnetic field from the coil. The coil 555 is placed as close as physically practical to the tissue, and its diameter is chosen such that the signal received by the probe lies primarily in the region under investigation. The spectroscopy coil 555 has been configured for $^{31}$P (2.4 T) using a standard tuning circuit. The coil 555 may be tuned for use with $^{31}$C, $^{23}$Na, and $^{19}$F by simply changing capacitor values. A dual-turn spectroscopy coil 555 is used in this case because the inductance of a single turn coil is too small to easily match with available standard capacitors.

The size and position of the proton coil 535 have been chosen so that the entire extent of the frozen region can be imaged. The same surface probe principles mentioned above apply here, though the problem of signal-to-noise is clearly not as important for the proton coil as for the spectroscopic coils since the abundance of protons is much greater than that of phosphorous-31 or sodium-23 atoms.

FIGS. 11a through 11r show a time sequence of radio frequency spoiled gradient echo images taken with the surface probe 500 of the present invention in contact with the surface of a 50 millimolar H$_3$PO$_4$ gelatin. In each image it takes about 25 seconds to acquire and process the data. The dark circle clearly visible in FIGS. 11a through 11k is a rod cross section having a diameter of 2.5 mm. The bead is 4 mm from the surface of the gelatin which appears as the dark border to the left of the image in FIG. 11a. FIGS. 11a through 11r show the gel 0, 31, 61, 91, 121, 151, 181, 215, 252, 285, 313, 348, 373, 404, 461, 501, 536, and 570 seconds, respectively, after the initiation of the flow of cryogen. The position of the dark left hand border in FIGS. 11g and 11h clearly begins to advance towards the rod, and after 4 minutes and 45 seconds, as shown in FIG. 11j, the interface appears to contact the rod. After 5 minutes 35 seconds the flow of cryogen was discontinued, but as evidenced by FIGS. 11l through 11o the interface continues to propagate.

The usefulness of the probe 500 in the treatment of skin cancer is demonstrated by generating a cryolesion on the femur of a rabbit. The probe 500 was placed in contact with an ex vivo (approximately 30 hrs old) rabbit leg on the upper half of the femur and placed in a 2.4 T (100 MHz) small bore NMR. After electronic shimming on the sample, baseline T1 weighted 200 μm×200 μm resolution images were taken (TR 30 ms, TE1 14.3 ms). Coolant was then turned on, and a series of two-dimensional spoiled gradient echo images were taken during the freezing process.

FIGS. 12a–12d show a 5.12 cm×5.12 cm field of view of the rabbit leg 850. In FIG. 12a the flow of liquid nitrogen has just begun and no freezing interface is visible. In FIG. 12b the flow of liquid nitrogen has been shut off after 7 minutes and 21 seconds, the frozen region 852 emits no signal and is therefore dark, and the freezing interface 855 is approximately a circular arc. FIG. 12c shows the rabbit leg 850 thirteen minutes and 43 seconds after the flow of liquid nitrogen was initiated. At this time the freezing interface 855 has propagated to a maximum distance within the leg 850. FIG. 12d shows the rabbit leg 850 twenty-six minutes and thirteen seconds after the flow of liquid nitrogen was first initiated. At this point the previously frozen region 852 has just completed thawing.

This particular configuration of probe and surface coil shows good image uniformity and sufficient signal-to-noise as far as 10 mm from the bottom of the probe surface when using fast spin-echo sequences. The 58 mm diameter surface coil provides sufficient image uniformity across the 53 mm field of view, but diminishes significantly outside of this. Alternatively, larger coils may be used for increased depth penetration and lateral extent, but the signal-to-noise sacrificed will at some point will be of an extent that 160 ms TR spin echo images are no longer feasible.

All of the techniques for determining the precise location of the boundary between tissue and cryolesion during cutaneous cryosurgery have to date depended on a significant amount of best guess judgement and experience of the surgeon. However, the extent of the region may be changed by any one of several factors including local areas of fat inside the region, increased blood flow caused by the induced cold injury near the Cryo lesion, and other factors including the proximity of nearby blood vessels which reduce the interface velocity near their location. The most common method of instrumentation is the needle mounted thermocouple, but even this has the disadvantage of giving temperature in only point locations; the actual lesion shape must be extrapolated from these measurements.

The probe 500 of the present invention is useful for cases where tumors are particularly deep and/or malignant and so require extra care to be certain that the entire extent of the cancerous region has been contained. In addition it is useful in areas around blood vessels which can change the expected pattern of the cryolesion.

Imaging of Prostate Surgery

To demonstrate the feasibility of magnetic resonance imaging for internal surgery, prostate surgery has been performed on a dog. The experimental protocol is as follows: An adult male mongrel dog is pre-anesthetized with an intravenous injection of sodium thialmylal, intubated, and placed on a ventilator. Anesthesia is maintained using methoxyflurane (MOF/N$_2$O/O$_2$) gasses and the body temperature is monitored throughout the experiment in order to maintain the dog as physiologically normal as possible. Imaging is conducted in a 1 meter diameter, warm bore Oxford magnet with the dog secured in the supine position. Prior to inserting the cryoprobe, sagittal and transverse scout spin-echo images are acquired for slice localization.

Magnetic resonance imaging has the advantage of providing a real-time three-dimensional view of the freezing process. Equipment associated with the technique must be compatible with large magnetic fields and radio frequency (RF) monitoring. In general, metallic cryosurgical probes are not compatible with large magnetic fields since most metals are paramagnetic and would serve as an RF antenna and disturb the signal. The cryoprobe of the present invention uses either a completely nonmetallic material such as Pyrex, or a metallic but nonmagnetic material such as brass or aluminum. In general, any existing probe configuration will also work with nonmetallic, or metallic but nonmagnetic or weakly magnetic compounds. The fact that long (30 cm) metallic probes (nonmagnetic) can work in the prostate increases significantly the range and possibilities of using cryosurgery with MRI.

The diameter cryoprobe used for the cryosurgical procedure is shown in the cross-sectional side and end views of FIGS. 6a and 6b. The cryosurgical probe 600 is 30 cm in length from the intracorporeal end 602 to the extracorporeal end 604. It is constructed from three concentric brass tubes 610, 620 and 630, with outside diameters of 0.159, 0.381, and 0.476 cm, respectively. Each tube 610, 620, and 630 is 0.356 mm thick. The tubes 610, 620 and 630 are ungrounded to prevent currents from flowing through the probe 600 in response to time-varying magnetic fields. The three tubes 610, 620 and 630 are held concentrically by small teflon spacers 606 placed in the gaps 615 and 625 between the tubes 610, 620, and 630, as is shown in FIG. 6b. The inner tube 610 is open ended at both ends. The middle tube 620 is closed at the intracorporeal end 602, and extends past the inner tube 610 at the intracorporeal end. At the extracorporeal end of the probe 600 the middle tube 620 is sealed to the inner tube 610 and the inner tube 610 extends past the end of the middle tube 620. Liquid nitrogen is supplied to the tip 602 of the cryoprobe 600 via a reducing "T" 670 at the extracorporeal end of the innermost tube 610. The vertical section of the reducing T 670 has an inner diameter of 0.63 cm. A gap 615 between the innermost tube 610 and middle tube 620 allows for liquid and/or gaseous nitrogen to exhaust through an exhaust outlet 640 located 2 cm from the extracorporeal end 604 of the middle tube 620. The middle tube 620 extends past the outer tube 630 at both the intracorporeal and extracorporeal ends, and the outer tube 630 is sealed to the middle tube 620 at both ends. As shown in FIG. 6b (but omitted from FIG. 6a for clarity), sheets of insulating mylar 627 with thickness of 0.25 mil are placed between spacers 606 in the gap 625 between the middle tube 620 and the outer tube 630. The region 625 between the outermost tube 630 and the middle tube 620 is then evacuated of gases through an evacuation tube, which becomes evacuation stub 650 when sealed, to increase the thermal insulation provided by the gap 625. The region of the middle tube 620 past the extracorporeal end of the outer tube 630 is uninsulated and is therefore the active region 608 of the probe. Silicone rubber tubes convey liquid nitrogen from a dewar to the probe 600, and from the exhaust outlet 640 to a locality away from the surgery. Connections to both the supply inlet and the exhaust outlet 640 are made via using Swageloc™ connectors. It is important to note that the functionality of this probe illustrates that ungrounded nonferromagnetic metals may be used to construct MRI compatible probes, even if the probe is quite long.

The cryoprobe 600 is inserted into the left lobe of the prostate using a standard surgical introducer-dilator technique under freehand control because the symphysis pubis in the dog prevented use of a transperineal biopsy guide. First, an NMR compatible 18-guage biopsy needle is inserted into the prostate and a floppy wire inserted through the needle. The needle is then withdrawn and a small introducer is inserted over the wire. Successively larger introducers are inserted until one which can accommodate the 0.476 cm cryoprobe 600 is introduced. At each appropriate stage, the correct positions of the introducer, dilator, and cryoprobe are verified using NMR images. Test using a variety of metals show that single small diameter (<0.5 cm) brass tubing produces a sufficiently small magnetic susceptibility artifact in the NMR images that cryoprobes constructed from this material can be used in the NMR magnet without substantial degradation of the images.

Once the cryoprobe 600 is in position, baseline $T_1$- and $T_2$-weighted images are acquired using spin-echo pulse sequences ($T_1$-wtd: $TE_1$=33 ms, TR=200 ms; $T_2$-wtd: $TE_1$= 33 1100 ms, TR=2000 ms). Imaging of the freeze/thaw cycle begins simultaneously with liquid nitrogen flow and continues throughout the freeze/thaw cycle. A sufficiently high liquid nitrogen flow is maintained through the probe 600 that liquid nitrogen drips continually from the exhaust line, thus insuring the lowest possible temperature of the active region 608 of the probe 600. A single freeze/thaw cycle is induced with the freezing portion lasting approximately 7 minutes, and the thawing portion lasting approximately 8 minutes. $T_1$-weighted images are acquired approximately every 1.1 minutes. When the images indicate that the right lobe of the prostate was frozen (7 minutes of freezing) liquid nitrogen flow is stopped and the prostate is allowed to thaw. After thawing, a final set of images are acquired, and the prostate excised and fixed in a 10% buffered formalin solution for later histologic analysis.

FIGS. 7a through 7g shows a time sequence of images acquired during the prostate cryosurgery. FIG. 7a shows a $T_1$-weighted spin-echo transverse section of the dog abdomen. The cryoprobe 600, inserted in the left lobe 804 of the prostate 800 slightly lateral to the center of the lobe, is visible. (In FIGS. 7a–7g, left and right is reversed.) The prostate 800 in the square region in the center of FIG. 7a is shown magnified in FIGS. 7b through 7g. The prostate in the 23 kg dog is approximately 1.8 cm in width and 2.5 cm in length, and is easily located in the NMR images. FIGS. 7b, 7c and 7d show the prostate 800 before freezing is initiated, 3 minutes after freezing has been initiated, and 7 minutes after freezing has been initiated, respectively. After 7 minutes of freezing, the cryolesion, visible as a large dark region, encompassed most of the left lobe 804 and extends 1–2 mm into the fatty tissue surrounding the prostate 800. FIGS. 7e, 7f and 7g show the prostate 3 minutes, 15 minutes and 30 minutes, respectively, after thawing begins. The thawing is complete after approximately 9.5 min. In FIG. 7f the probe 600 has been removed. As shown in FIG. 7g, 30 minutes after thawing is complete there is evidence of edema in the left lobe 804 of the prostate 800 as indicated by an increase in signal intensity in both the proton density and $T_2$-weighted images. Analysis of $T_2$-weighted imaging (not shown here) shows that the increased signal also extends approximately 2 mm laterally outside the parenchyma of the prostate 800.

The prostate is then sectioned in a plane corresponding to the NMR imaging plane and prepared for histologic analysis after one week of fixing the prostate in a 10% formalin solution. The gross lesion appeared as a dark hemorrhagic semicircular region encompassing 90% of the lateral portion of the prostate's left lobe 804, as shown in FIG. 8a, is clearly distinguishable from the unaffected portion in the right lobe 802 of the prostate 800. Histologically, the central part of the lesion is hemorrhagic, edematous and completely necrotic. As shown in FIG. 8b, the boundary of the lesion 803 between the hemorrhagic tissue 805 and the healthy tissue 801 is sharp, having a width of less than 0.7 mm. At the lesion's boundary 803, the stroma, vascular bed and myoepithelial cells are intact but the glandular cells are destroyed. Evidence of inflammation is indicated by the presence of sparse infiltrated neutrofils in the stroma of the lesion's boundary 803.

Comparison of FIGS. 8a and 7d shows that the location of the lesion is accurately represented by the NMR images. The NMR images at the end of freezing indicate that the cryolesion has encompassed almost all of the left lobe 804 of the prostate 800. In addition, evidence of edema is supported by the histologic findings. The boundary of the cryolesion is readily apparent in the NMR images and corresponds to the location of the boundary in the histologic sections. The resolution of the NMR images is 1 pixel/mm so the accuracy of determining the exact location of the freezing boundary is on the order of 1 mm. Better resolution can be obtained by using a higher pixel density or placing the coil on the probe. The fact that the boundary between necrotic and undamaged tissue is so sharp indicates that NMR images are useful in predicting damage from the location of the freezing interface. By monitoring the growth of frozen tissue, the freezing can be stopped when the freezing interface reaches the boundary of the prostate. Therefore a predictable volume of destroyed tissue can be observed in the NMR images.

Interactive control of cryosurgery with NMR

Freezing can be used both for the preservation of, and the destruction of, biological tissues. The results of the process of freezing and subsequent thawing depend on the thermal history during the process. Though NMR can be used to determine the position of the freezing interface, NMR is unable to monitor thermal events in the frozen region itself. However, the temperature inside the frozen region can be calculated using analytical solutions of the energy equation.

In general, the solution of the heat transfer equation with phase transformation is difficult because the position of the freezing interface as a function of time is unknown prior to the solution. This introduces a nonlinearity in the problem, making it difficult to solve. However, when the position of the freezing interface is known, the problem becomes simple and can be solved by a variety of methods. Imaging the position of the freezing interface with NMR, and incorporating this information in the energy equation transforms this problem from one of the more difficult problems of heat transfer into a relatively simple one. The energy equation is $$\nabla^2(k\nabla T) = \rho c \frac{\partial T}{\partial t}$$

where k is the thermal conductivity, ρ is the density, c is the heat capacity, T is the temperature, and t is time.

In the NMR-based heat transfer model we need to solve the energy equation in the frozen region only since the heat transfer problem is completely specified when the geometry of the boundary and the temperatures on it are known. NMR images will provide the coordinates of the boundary, i.e., the cryoprobe surface and the freezing interface. The boundary temperatures are the probe temperature, which is known through thermistor or optical thermometry measurements (using, for example, the Luxtron Model 3000 fluoroptic 8 channel system) and the phase transition temperature on the freezing interface which is approximately −0.56 C. The enthalpy finite element method or the finite difference method (see Glen E. Myers "Analytical Methods in Conduction Heat Transfer," Genium Publ. Co. Schenectady, N.Y., 1982) can be used to solve the energy equation. Because knowing the location of the freezing interface simplifies this problem, the computer program can be implemented on a work station and run in real time. The problem of finding sufficiently rapid techniques for solution is aided by the fact that during cryosurgy freezing occurs slowly. The freezing interface velocity is on the order of 1 mm/min. The accuracy of the solution is also very good because once tissue is frozen its properties are essentially completely specified by the water content of the specific tissue and the thermal properties of ice. The calculated temperature distribution can then be plotted on the imaging monitor as isotherms, or the temperature history at any point can be correlated to known criteria for physiological damage to indicate regions that are destroyed or regions that are spared from freezing damage according to these criteria.

During cryosurgery, the region adjacent to the frozen tissue will also experience a temperature drop. This temperature drop may, by itself, be detrimental to the biological tissue. This has been confirmed in the experiments with the brain. Therefore, the temperature information in the unfrozen tissue may be important in developing control algorithms for cryosurgery.

The temperature in the unfrozen region can be directly monitored from T1-weighted NMR images. The T1 of tissues is approximately proportional to temperature in degrees Celsius, i.e., T1 is proportional to (a +0.0074 T), where a is a constant that depends on the tissue [Bottomley et al., "A review of $^1$H NMR relaxation in pathology; are $T_1$ and $T_2$ diagnostic?" Mechanical Physics, 14(1), 1–37, 1987] and T is temperature. The constant a is approximately 0.53 for brain tissue at 2 Tesla. Inversion Recovery (IR) experiments provide a sensitive measure of T1 and therefore temperature. The NMR signal generated in an IR experiment with a long relaxation time TR is proportional to [1–2 exp (TI/T1)], where TI is the inversion recovery period. The relationship for IR-RARE will be slightly more complicated because the condition TR >>TI is not satisfied. If TI is taken as the T1 at 37° C., then the temperature dependence of the IR signal is approximately $$1-2\exp(-1/(1+0.01T)) \approx 0.264 - 6.57 \times 10^{-3} T \quad (4)$$

over the temperature range of 0° C. to 40° C. Therefore, there is approximately a five-fold increase in signal intensity as one moves from the metabolic tissue temperature of 37° C. toward the freezing interface at T≈−0.57° C.

Studies on gelatin phantoms demonstrate the ability of IR-RARE [Mulkern et al., "Contrast Manipulation and Artifact Assessment of 2D and 3D RARE sequence," *Magnetic Resonance in Medicine* 8, 557–566 (1990)] to measure the one-dimensional temperature distribution in unfrozen regions using a three-chamber apparatus. The outer two chambers are held at two different temperatures by circulating fluids, and the gelatin is placed in the center chamber. The temperature in one outer chamber is held at 20° C. while the temperature in the other is decreased stepwise to −10° C. in 2° C. intervals. Heat transfer theory predicts that at thermal equilibrium, the temperature will have a linear temperature profile across the gelatin. At each step the gelatin was allowed to come to thermal equilibrium before proceeding to the next, thus establishing a series of known temperature gradients in the gelatin. MR images using IR-RARE (T1=800 ms; recycle delay=2 sec; 31 echoes) are acquired both during cool down and during freezing. With this inversion time T1, the signal intensity decreases as temperature increases. FIG. 9 shows the signal intensity versus temperature taken from a two-dimensional IR-RARE image of the gel with one end held at 0° C. and the other at 20° C. The temperatures are measured by thermocouples in the gel. A linear temperature gradient is expected. A second order polynomial is fit to the data. Alternatively, a model based on the spin dynamics of the IR-RARE experiment may be employed. The correlation between theory and experiment in FIG. 9 indicates that IR-RARE experiments can achieve high accuracy in the temperature range of interest for cryosurgery.

During slow one-dimensional freezing (≈0.5 mm/min) the gelatin remains in thermal equilibrium because the heat transfer rate in the gelatin is much higher than the freezing rate. A zeroth order perturbation solution for the temperature distribution, T(x) in the unfrozen gelatin is:

$$T(x) = (T_{ph}a - T_H s(t))\frac{s(t)}{a - s(t)} + (T_H - T_{ph})\frac{x}{a - s(t)},$$

where $T_{ph}$ is the phase transition temperature (0° C.), $T_H$ is the temperature of the hot side (20° C.), a is the thickness of the sample (25 cm), s(t) the thickness of the ice, and x is the distance along the direction of freezing starting from the cold side. For the case studied this equation reduces to:

$$T(x) = 20 \cdot \frac{1+x}{0.025 - s(t)}.$$

Therefore a linear temperature distribution in the unfrozen gelatin is expected. FIG. 10a shows signal intensity versus position, 8 minutes and 14 minutes after the gel begins to freeze. No signal is detected from the frozen gel, so the position of the interface is easily located.

FIG. 10a shows temperature distributions calculated by using the curve in FIG. 9 as a calibration. Data for the 7 mm thick ice sample are shown along with the line predicted by theoretical calculation 10b. The plotted points in FIG. 10b start at the boundary of the frozen gel. Overall, there is agreement with the IR-RARE experiments within the accuracy of the zeroth order theoretical solution. The IR-RARE experiments showed a linear temperature increase across the unfrozen gelatin. A line is drawn through the points in FIG. 10b to indicate the linearity. The basic relations for predicting the temperature in other tissues types are the same.

NMR interactive cryosurgery control

One of the problems associated with cryosurgery is the control of the freezing interface propagation. Lack of control can result in undesirable freezing of sensitive tissue, particularly when multiple probes are used. NMR-monitored interactive cryosurgery can provide surgeons with information during the procedure that can facilitate more accurate application of the procedure to compensate for errors in the treatment planning process, thereby avoid over-freezing or under-freezing, and assuring a freezing protocol that results in assured destruction of tissue. The method of the present invention employs a system that monitors the position of the freezing interface and the temperature in the unfrozen region using NMR, calculates the temperature distribution in the frozen region as described in the previous section and the velocity of the freezing interface, and displays this additional information superimposed on the NMR slices. Although cryosurgical probes may not be moved during the freezing process, their temperature can be adjusted to achieve a desirable thermal history or freezing interface velocity. By observing the progress of the frozen region and the temperature distribution in the tissue the flow of cryogen or its temperature can be adjusted to achieve a desired result either through manual control by the surgeon or though an online feedback control system.

The technique to determine the velocity of the freezing interface uses the M-based temperature model in the frozen region described above and the NMR measurement of the temperature in the unfrozen region also described above. (The temperature in the unfrozen region is obtained from NMR thermometry. The temperature in the frozen region is obtained by solving the NMR-based heat transfer model.) The position and velocity of the interface (calculated from the temperature gradient) is obtainable from a single IR-RARE image which provides complete dynamic characterization. The temperature distributions can be used with Fourier's law to determine heat fluxes at the freezing interface. Thereafter, the velocity of the freezing interface can be determined by solving the equation $q_u \text{-} q_f = \rho_o \cdot L \cdot v_n$ where $q_u$ is the heat flux in the unfrozen region, $q_f$ is the heat flux in the frozen region, $\rho_o$ is the density, L is the latent heat of fusion, and $v_n$ is the required velocity of the freezing interface. The velocity of the interface is used to determine if a particular sensitive tissue is in imminent danger of being frozen.

In summary, apparatus and methods for magnetic resonance assisted cryosurgery have been described.

The present invention has been described in terms of a preferred embodiment. The invention, however, is not limited to the embodiment depicted and described. Many variations are within the scope of the invention. For instance, the need to visualize the process of freezing inside tissue is not limited only to cryosurgery, but is also important in any other application where biological materials are frozen. Therefore, another application is preservation of biological materials in medicine and biotechnology, such as cells, cells in suspension, tissues, such as pancreatic islets, skin, whole organs or even whole animals, by freezing or vitrification. Another application is monitoring the process of freezing during preservation of foods such as meat, fish, vegetables, fruit, or dough. Furthermore, the need to monitor tissue damage is useful for surgical and medical purposes other than cryosurgery, such as laser surgery and radiation therapy. Other variations within the scope of the present invention include: minimization techniques other than the downhill simplex method may be used to determine an optimal placement of the cryoprobes and the optimization of other parameters of the cryosurgery; the temperature histories of the cryoprobes may be held constant while the positions of the cryoprobes are optimized; the positions of the cryoprobes may be held constant while the temperature histories of the cryoprobes may be optimized; the stereotactic device may be constructed of other materials, including plexiglass, fiberglass, plastic, rubber, etc.; the dimensions of the cryoprobe and coils are not special or unique and numerous other dimensions and configurations with coils attached to the probe are possible; the stereotactic device may hold a plurality of probes; the stereotactic device may incorporate other means for positioning and securing the cryoprobes; radio frequency coils may be positioned in the cryosurgical region without being attached to the cryoprobe or cryoprobes; the stereotactic device may utilize a different configuration of the position/orientation markers; the probe of the present invention can be used with a variety of surgical techniques, such as cauterization, heating, cooling, laser treatment or mechanical resection, suction and other alterations of tissue; tissue damage may be monitored using nuclei other than phosphorus-31 and sodium 23; the cryogen is not limited to liquid nitrogen; the temperature distribution in the freezing region may be calculated without using T1 data; or the MR coil may be mounted on the cryoprobe in a different manner, at a different location, or in a different orientation.

Rather, the scope of the invention is defined by the appended claims.

What is claimed is:

1. A method for monitoring temperatures of a target region in a biological tissue with a magnetic resonance imaging technique and a cryoprobe, said target region including a frozen region having a first temperature distribution, an unfrozen region having a second temperature distribution, and an interfacial surface bounding said frozen region, comprising the steps of:

generating an image of said target region with said magnetic resonance imaging technique;

determining the location of said frozen region using the image so generated;

determining a temperature at said interfacial surface;

solving a heat equation for the interior of said frozen region utilizing the temperature at said interfacial surface to determine said first temperature distribution in said frozen region;

determining said second temperature distribution in said unfrozen region, and using said first and second temperature distributions determined to monitor the temperature of said target region.

2. The method of claim 1 further comprising accomplishing the step of determining the location of said frozen region by correlating a region that generates a low magnetic resonance signal with said frozen region.

3. The method of claim 2 further comprising the step of displaying said magnetic resonance image and said first temperature distribution.

4. The method of claim 2 further comprising the step of displaying said magnetic resonance image and said second temperature distribution.

5. The method of claim 2 wherein said interfacial surface includes the surface of said cryoprobe.

6. A method for utilizing information obtained from magnetic resonance imaging of a target region to control real-time cryosurgical parameters, said target region including a frozen region having a first temperature distribution, an unfrozen region having a second temperature distribution, and an interfacial surface bounding said frozen region, comprising the steps of:

generating an image of said target region with a magnetic resonance imaging technique;

identifying said frozen region as a section of the image so generated having no magnetic resonance signal;

determining a temperature at said interfacial surface;

solving the heat equation for the interior of said frozen region utilizing a temperature at said interfacial surface to determine said first temperature distribution in said frozen region;

measuring nuclear relaxation times in said unfrozen region by a magnetic resonance technique;

determining said second temperature distribution in said unfrozen region by calculations based on said nuclear relaxation times as measured by said magnetic resonance technique; and affecting said cryosurgical parameters according to said first and second temperature distributions to achieve a desired result.

7. The method of claim 6 wherein said cryosurgical parameters include a flow of cryogen to a cryoprobe.

8. The method of claim 6 further comprising the step of displaying said magnetic resonance image and said first temperature distribution.

9. The method of claim 6 further comprising the step of displaying said magnetic resonance image and said second temperature distribution.

10. A method for monitoring temperatures of a target region in a biological tissue with a magnetic resonance imaging technique and a cryoprobe, said target region including a frozen region having a first temperature distribution, an unfrozen region having a second temperature distribution, and an interfacial surface bounding said frozen region, comprising the steps of:

generating an image of said target region with said magnetic resonance imaging technique;

identifying said frozen region as corresponding to a section of the image so generated having a low magnetic resonance signal;

determining a temperature at said interfacial surface;

solving a heat equation for the interior of said frozen region utilizing the temperature at said interfacial surface to determine said first temperature distribution in said frozen region;

measuring nuclear relaxation times in said unfrozen region by a magnetic resonance technique;

determining said second temperature distribution using calculations based on said nuclear relaxation times measured in said unfrozen region; and using said first and second temperature distributions determined to monitor the temperature of said target region.

11. The method of claim 10 wherein said magnetic resonance technique is a spoiled radio frequency technique.

12. The method of claim 10 wherein said magnetic resonance technique is a spin-echo technique.

13. A method for monitoring temperatures of a target region in a biological tissue with a magnetic resonance imaging technique and a cryoprobe, said target region including a frozen region having a first temperature distribution, an unfrozen region having a second temperature distribution, and an interfacial surface bounding said frozen region, comprising the steps of:

generating an image of said target region with said magnetic resonance imaging technique;

determining the location of said frozen region using the image so generated;

solving a heat equation for the interior of said frozen region using a temperature of approximately −0.56 degrees Celsius as the temperature at said interfacial surface to determine said first temperature distribution in said frozen region;

determining said second temperature distribution for said unfrozen region; and using said first and second temperature distributions determined to monitor the temperature of said target region.

14. The method of claim 10, wherein said temperature at said interfacial surface is determined by the composition of said biological tissue and thermodynamic phase equilibrium at the interface.

* * * * *